United States Patent
Sanders et al.

(10) Patent No.: US 11,147,910 B2
(45) Date of Patent: Oct. 19, 2021

(54) PACKAGING FOR SAFETY NEEDLE

(71) Applicant: Becton, Dickinson and Company, Franklin Lakes, NJ (US)

(72) Inventors: Laurie Sanders, Glen Ridge, NJ (US); Edward P. Browka, Oneida, NY (US); Peter Smith, Cary, NC (US); Adam Kristopher Brakoniecki, Hawthorne, NJ (US); Alice Wong, Leonia, NJ (US); Regina Haywood, Franklin Lakes, NJ (US); Eli B. Nichols, Durham, NC (US); Robert Henson, Fuquay Varina, NC (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 54 days.

(21) Appl. No.: 15/837,020

(22) Filed: Dec. 11, 2017

(65) Prior Publication Data
US 2018/0161492 A1 Jun. 14, 2018

Related U.S. Application Data

(60) Provisional application No. 62/533,786, filed on Jul. 18, 2017, provisional application No. 62/533,837, (Continued)

(51) Int. Cl.
*A61M 5/00* (2006.01)
*A61M 5/32* (2006.01)

(52) U.S. Cl.
CPC .......... *A61M 5/002* (2013.01); *A61M 5/3202* (2013.01)

(58) Field of Classification Search
CPC ...... A61M 5/002; A61M 5/003; A61M 5/008; A61M 5/00; A61M 5/3202; A61M 5/3204; A61M 5/3205; A61M 5/32
See application file for complete search history.

(56) References Cited

U.S. PATENT DOCUMENTS 2,023,289 A 12/1935 Pringle
2,557,222 A 6/1951 Goode
(Continued)

FOREIGN PATENT DOCUMENTS

CA 2551835 A1 8/2005
EP 0734739 A2 10/1996
(Continued)

OTHER PUBLICATIONS

PCT Invitation to Pay Additional Fees, and, Where Applicable, Protest Fee in PCT/US2017/065718 dated Apr. 9, 2018, 13 pages.
(Continued)

*Primary Examiner* — Steven A. Reynolds
*Assistant Examiner* — Javier A Pagan
(74) *Attorney, Agent, or Firm* — Servilla Whitney LLC

(57) ABSTRACT

Packaging for safety needle devices are described herein. Such packaging can include hard packaging for safety needle devices. Such packaging can include a cavity or recess in a compartment of the packaging to house an activation element of a safety needle device to prevent accidental activation of the safety needle device prior to use by the user. Such packaging can include a cavity or recess in a safety needle device to house an activation element located on the inside surface of the compartment of the packaging to prevent accidental activation of the safety needle device prior to use by the user.

30 Claims, 21 Drawing Sheets

Related U.S. Application Data filed on Jul. 18, 2017, provisional application No. 62/479,507, filed on Mar. 31, 2017, provisional application No. 62/479,563, filed on Mar. 31, 2017, provisional application No. 62/433,044, filed on Dec. 12, 2016.

(56) References Cited

U.S. PATENT DOCUMENTS

| | | | |
|---|---|---|---|
| 3,367,488 A * | 2/1968 | Hamilton | A61M 5/002 206/365 |
| 3,485,416 A | 12/1969 | Fohrman | |
| 3,869,062 A | 3/1975 | Jaeschke et al. | |
| 3,934,722 A | 1/1976 | Goldberg | |
| 4,184,593 A | 1/1980 | Dorr | |
| 4,610,667 A | 9/1986 | Pedicano et al. | |
| 4,950,242 A | 8/1990 | Alvarez | |
| 5,084,027 A | 1/1992 | Bernard et al. | |
| 5,084,028 A | 1/1992 | Kennedy et al. | |
| 5,330,899 A | 7/1994 | Devaughn | |
| 5,336,197 A | 8/1994 | Kuracina et al. | |
| 5,336,199 A | 8/1994 | Castillo et al. | |
| 5,415,645 A | 5/1995 | Friend et al. | |
| 6,880,701 B2 | 4/2005 | Bergeron et al. | |
| 7,134,550 B2 | 11/2006 | Groth | |
| 7,320,682 B2 | 1/2008 | Cocker et al. | |
| 7,665,605 B2 | 2/2010 | Erickson et al. | |
| 7,871,397 B2 | 1/2011 | Schraga | |
| 8,048,036 B2 | 11/2011 | Woehr et al. | |
| 8,133,200 B2 | 3/2012 | Dibiasi et al. | |
| 8,579,115 B2 | 11/2013 | Murphy et al. | |
| 8,763,826 B1 | 7/2014 | Smith et al. | |
| 2001/0031949 A1 | 10/2001 | Asbaghi | |
| 2002/0063074 A1 | 5/2002 | Simm et al. | |
| 2002/0165497 A1 | 11/2002 | Greene | |
| 2003/0015444 A1 | 1/2003 | Molin et al. | |
| 2003/0093009 A1 | 5/2003 | Newby et al. | |
| 2003/0120209 A1 | 6/2003 | Jensen et al. | |
| 2003/0121815 A1 | 7/2003 | Bergeron et al. | |
| 2003/0181867 A1 | 9/2003 | Bressler et al. | |
| 2003/0181869 A1 | 9/2003 | Swenson et al. | |
| 2004/0178098 A1 | 9/2004 | Swenson et al. | |
| 2005/0067309 A1 | 3/2005 | Choi | |
| 2005/0113750 A1 | 5/2005 | Targell | |
| 2005/0279664 A1 | 12/2005 | Hommann | |
| 2006/0189933 A1 | 8/2006 | Alheidt et al. | |
| 2006/0213793 A1 | 9/2006 | Brand | |
| 2009/0024093 A1 | 1/2009 | Carrel et al. | |
| 2009/0254042 A1 | 10/2009 | Gratwohl et al. | |
| 2009/0299295 A1 | 12/2009 | Rubinstein et al. | |
| 2011/0319817 A1 | 12/2011 | Rubinstein et al. | |
| 2012/0029440 A1 | 2/2012 | Boyd et al. | |
| 2012/0041380 A1 | 2/2012 | Chapin et al. | |
| 2012/0051967 A1 | 3/2012 | Murphy et al. | |
| 2012/0059331 A1 | 3/2012 | Dibiasi et al. | |
| 2012/0130342 A1 | 5/2012 | Cleathero | |
| 2014/0048433 A1 | 2/2014 | Dasbach et al. | |
| 2014/0076758 A1 | 3/2014 | Dasbach et al. | |
| 2014/0097111 A1 | 4/2014 | Dasbach et al. | |
| 2014/0364803 A1 | 12/2014 | Rubinstein et al. | |
| 2015/0034516 A1 | 2/2015 | Chapin et al. | |
| 2015/0165132 A1 | 6/2015 | Perot et al. | |
| 2015/0197393 A1 * | 7/2015 | Braun | B65D 25/10 206/497 |
| 2015/0297837 A1 | 10/2015 | Schraga | |
| 2015/0297881 A1 * | 10/2015 | Sanders | A61J 1/2055 604/535 |
| 2016/0074572 A1 | 3/2016 | Spool et al. | |
| 2016/0303331 A1 | 10/2016 | Evans et al. | |
| 2017/0106136 A1 | 4/2017 | Dibias | |
| 2017/0233168 A1 | 8/2017 | Horvath et al. | |
| 2018/0161490 A1 | 6/2018 | Sanders et al. | |
| 2018/0161492 A1 | 6/2018 | Sanders et al. | |
| 2018/0161521 A1 | 6/2018 | Sanders et al. | |

FOREIGN PATENT DOCUMENTS

| | | |
|---|---|---|
| EP | 0750915 A2 | 1/1997 |
| EP | 1537890 A1 | 6/2005 |
| EP | 1949928 A1 | 7/2008 |
| EP | 2298397 A1 | 3/2011 |
| FR | 2884723 A1 | 10/2006 |
| FR | 2930160 A1 | 10/2009 |
| GB | 2437923 A | 11/2007 |
| JP | 2007519474 A | 7/2007 |
| WO | 92/06725 A1 | 4/1992 |
| WO | 02/11797 A1 | 2/2002 |
| WO | 03/045480 A1 | 6/2003 |
| WO | 2008050158 A2 | 5/2008 |
| WO | 2009040602 A1 | 4/2009 |
| WO | 2010/033767 A2 | 3/2010 |
| WO | 2011/107330 A1 | 9/2011 |
| WO | 2012/000833 A1 | 1/2012 |
| WO | 2013073122 A1 | 5/2013 |
| WO | 2015/164416 A1 | 10/2015 |
| WO | 2016/087187 A1 | 6/2016 |

OTHER PUBLICATIONS

Non-Final Office Action in U.S. Appl. No. 15/837,018 dated Dec. 5, 2019, 14 pages.
Non-Final Office Action in U.S. Appl. No. 15/837,748 dated Oct. 17, 2019, 19 pages.
Non-Final Office Action in U.S. Appl. No. 15/837,756 dated Oct. 17, 2019, 39 pages.
Non-Final Office Action in U.S. Appl. No. 15/837,810 dated Oct. 17, 2019, 27 pages.
Final Office Action in U.S. Appl. No. 15/837,018 dated Jun. 18, 2019, 15 pages.
Non-Final Office Action in U.S. Appl. No. 15/837,012 dated Aug. 16, 2019, 14 pages.
Non-Final Office Action in U.S. Appl. No. 15/837,018 dated Nov. 6, 2018, 11 pages.
PCT International Search Report and Written Opinion in PCT/US2017/065718 dated Jan. 2, 2019, 18 pages.
PCT International Search Report and Written Opinion in PCT/US2017/065691 dated Mar. 27, 2018, 14 pages.
PCT International Search Report and Written Opinion in PCT/US2017/065692 dated Mar. 13, 2018, 14 pages.
PCT International Search Report and Written Opinion in PCT/US2017/065693 dated Mar. 7, 2018, 12 pages.
PCT International Search Report and Written Opinion in PCT/US2017/065716 dated Mar. 21, 2018, 14 pages.
PCT International Search Report and Written Opinion in PCT/US2017/065717 dated Mar. 19, 2018, 12 pages.
PCT International Preliminary Report on Patentability in PCT/US2017/065693 dated Jun. 27, 2019, 7 pages.
PCT International Search Report and Written Opinion in PCT/US2021/019381 dated Jun. 11, 2021, 18 pages.

* cited by examiner

PACKAGING FOR SAFETY NEEDLE

CROSS-REFERENCE TO RELATED APPLICATIONS

This application claims priority under 35 U.S.C. § 119(e) to U.S. Provisional Application No. 62/533,837, filed Jul. 18, 2017, U.S. Provisional Application No. 62/533,786, filed Jul. 18, 2017, U.S. Provisional Application No. 62/433,044, filed Dec. 12, 2016, U.S. Provisional Application No. 62/479,507, filed Mar. 31, 2017 and U.S. Provisional Application No. 62/479,563, filed Mar. 31, 2017, the disclosures of which are incorporated herein by reference in their entirety.

TECHNICAL FIELD

The present disclosure generally relates to packaging for medical devices, and more particularly to packaging for passive safety needles requiring axial or rotational movement of an element of the passive safety device for passive activation.

BACKGROUND

Clean or sterile articles particularly useful for medical applications are packaged to preserve their sterility. The packaging for these articles is intended to provide a barrier to prevent microorganisms from entering inside the packaging to contaminate its contents. In most instances, the packaging is opened immediately prior to using the article, such as a syringe or a needle, so as to minimize the time period in which the article is exposed to unsterile conditions.

Needle devices are used throughout the medical industry for the injection and withdrawal of a wide variety of fluids and solutions into and from the human body. Because of the numerous potential hazards associated with the handling and manipulation of bodily fluids, and particularly blood, passively activated safety features are frequently incorporated into various types of needle devices to protect the practitioner from accidental exposure to the needle.

Passive safety needle devices may include a retractable sheath and one or more retraction and locking elements which may also incorporate reuse prevention features. Incidental or accidental activation of the passive safety features may result from the movement of the safety needle device in the packaging during shipment or storage of the safety needle device thus rendering the safety needle device useless prior to use. Incidental or accidental activation of the passive safety features may also result from the packaged safety needle device being dropped which would also result in rendering the safety needle device useless prior to use.

Accordingly, there is a need for packaging of passively activated safety needle devices which prevents activation of the passively activation safety mechanism prior to intended use while also preserving the sterility of the passively activated safety needle devices. There is also a need to provide packaging to prevent unintended activation for passive safety needles that requiring axial or rotational movement of a element of the safety needle device for passive activation.

SUMMARY

One aspect of the present disclosure pertains to a medical packaging having an open proximal end, a closed distal end, and a compartment having a sidewall extending between the closed distal end and the open proximal end. In one or more embodiments, the medical packaging may also include one or more cavity projecting outwardly from the sidewall extending to the open proximal end in a distal direction along a portion or along the entirety of the length of the compartment. In one or more embodiments, the medical packaging also having a plurality of interference ribs disposed on the inside surface of the compartment and a flange disposed at open proximal end. In one or more embodiments, the plurality of interference ribs may be disposed on the inside surface of the one or more cavity projecting outwardly from the sidewall.

In one or more embodiments, the compartment having a first segment, a second tapered segment, and a third narrowed segment.

In one or more embodiments, the plurality of interference ribs extend radially inward from the sidewall and are configured to engage a portion of a fluid transfer device when the fluid transfer device is positioned within the interior cavity of the packaging.

In one or more embodiments, the one or more cavity may be disposed 180° apart. In one or more embodiments, the plurality of interference ribs extends in a direction substantially parallel to a longitudinal axis of the compartment.

The plurality of interference ribs may have a triangular, square, rectangular, or rounded shape.

In one or more embodiments, the medical packaging further includes a removable seal that interacts with the flange. The removable seal may include a pull tab. The removable seal may also include graphics, symbols, diagrams, words or other instructions. In one or more embodiments, the flange may have at least one flat edge.

In one or more embodiments, the plurality of interference ribs may be positioned equi-distance about the circumference of the inside surface of the cavity.

In another embodiment, the plurality of interference ribs may be oriented 180° apart around a circumference of the inside surface of the cavity.

In one or more embodiments, the plurality of interference ribs may be arranged in sets of two or more individual ribs. The individual ribs comprising the one or more sets of interference ribs may be spaced close together from one another. In an alternate embodiment, the individual ribs comprising the one or more sets of interference ribs may be spaced apart from one another.

In one or more embodiments, the interference ribs may be configured to engage a portion of a body of a safety needle device via friction-fit.

In one or more embodiments, the plurality of interference ribs may be disposed along a portion or the entire length of the inner surface of the compartment.

In one or more embodiments, the plurality of interference ribs may be made from a polymeric material. The polymeric material may be polyester, polycarbonate, polyethylene, polystyrene, polypropylene, or combinations or co-polymers thereof.

In one or more embodiments, the plurality of interference ribs may be oriented opposite from each other around a circumference of the packaging.

In one or more embodiments, the cavity is shaped to nest a protruding segment of a body of a safety needle device.

The medical packaging may further include a short rib disposed in an off-center orientation on the inside surface of the compartment.

The medical packaging may also further include an activation prevention element disposed on the inner surface of the compartment. In one or more embodiments, the activation prevention element may be disposed on the inner surface of the compartment extending between the closed distal end and the third narrowed segment of the compartment. The activation prevention element may be configured to engage with a corresponding slot, notch or recess located on an activation element of a safety needle device. The activation element of the safety needle device may be passively activated. The activation element of the safety needle device may also move axially, rotationally or both axially and rotationally.

In one or more embodiments, the activation prevention element may be in the form of ribs protruding outwardly into the cavity of compartment.

In one or more embodiments, the activation element may be configured to nest a passive activation element of a safety needle device. In one or more embodiments, the activation element may be configured to nest a passive rotational activation element of a safety needle device. In one or more embodiments, the activation prevention element may include a tapered leading edge.

The medical packaging may further include a clearance between the closed distal end and a distal tip of a safety needle device when the safety needle device is fully positioned in the medical packaging.

In one or more embodiments, the medical packaging may further include at least one external rib extending radially outward from the sidewall.

Another aspect of the present disclosure pertains to a medical packaging system including a safety needle device having a passive activation element; and a hard package having an open proximal end, a closed distal end, a compartment having a sidewall extending between the closed distal end and the open proximal end; one or more cavity projecting outwardly from the sidewall extending to the open proximal end in a distal direction along a portion or along the entirety of the length of the first segment of the compartment; a plurality of interference ribs disposed on the inside surface of the cavity; and a flange disposed at open proximal end. In one more embodiments, the compartment may include a first segment, a second tapered segment, and a third narrowed segment. In one or more embodiments, the cavity may be rectangle shaped.

In one or more embodiments, the safety needle device may be a passive safety needle or an active safety needle.

Another aspect of the present disclosure pertains to a medical packaging including an open proximal end, a closed distal end, a compartment having a sidewall extending between the closed distal end and the open proximal end, one or more molded detents on an inside surface of the compartment, and a flange disposed at the open proximal end.

DETAILED DESCRIPTION

Figure 1:
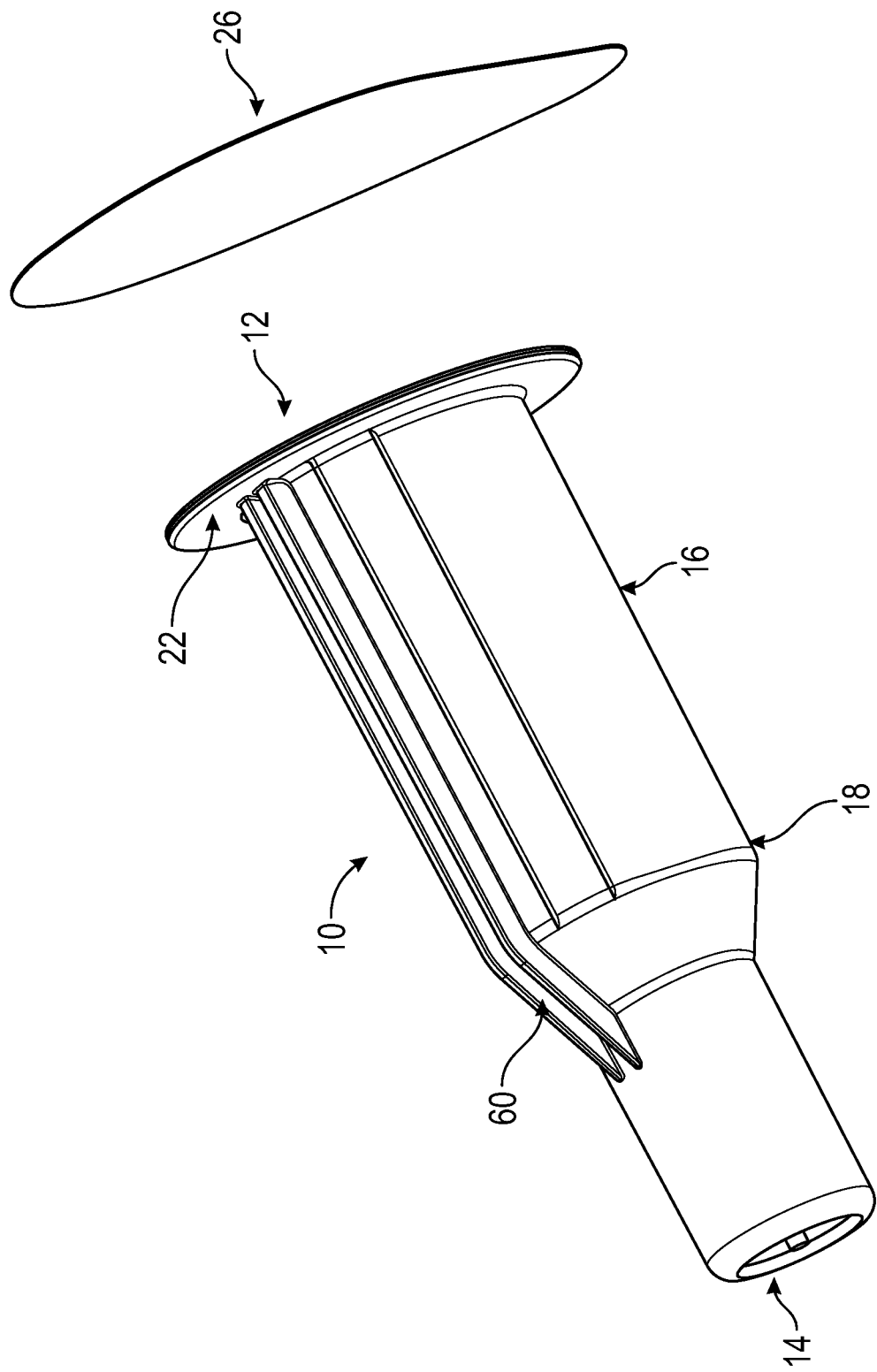
FIG. 1 is a perspective view of a single compartment packaging according to one aspect of the present disclosure.

Before describing several exemplary embodiments of the present disclosure, it is to be understood that the embodiments of the present disclosure are not limited to the details of construction or process steps set forth in the following description. The embodiments of the present disclosure are capable of other embodiments and of being practiced or being carried out in various ways.

With respect to terms used in this disclosure, the following definitions are provided.

As used herein, the use of "a," "an," and "the" includes the singular and plural.

Reference to "needle" includes needles that are suitable for filling and/or injecting liquids into or out of a syringe.

In this disclosure, a convention is followed wherein the portion of a device closest to the practitioner operating the needle safety device is termed "proximal" and the portion of the needle safety device toward the patient (for injection) or vial containing liquid (for filling) and farthest from the practitioner is termed "distal." In various embodiments, the needles described herein can be blunt fill needles, safety needles and/or conventional needles.

As used herein, a "fill needle" refers to a needle that is suitable to fill a syringe but may not be suitable for injection. For example, a fill needle may be a blunt needle that is not suitable to penetrate a patient's skin.

As used herein, a "safety needle" refers to a needle suitable for injection that includes one or more features to prevent needle stick injuries. In one or more embodiments, a safety needle includes a sheath that covers the distal end of the needle. As used herein, an "active safety needle" refers to a safety needle with a user-operated activation mechanism to cover the distal end of the needle after a patient has been injected. As used herein, a "passive safety needle" refers to a safety needle with a passive activation mechanism that automatically covers the distal end of the needle after a patient has been injected.

Any suitable needle devices comprising a safety feature may be used in conjunction with the packaging disclosed herein. Exemplary safety needle devices include, but are not limited to, those described in commonly owned, U.S. Patent Application Nos. 62/479,507 and 62/533,786, the disclosures of which are incorporated herein by reference in their entireties.

As used herein, the terms "package" or "packaging" includes any material used to wrap or protect a good or product, such as a syringe or a needle. Packaging can be rigid or flexible. Packaging includes, but is not limited to, medical packaging, pharmaceutical packaging, and child-resistant packaging. Medical and pharmaceutical packaging can include hard packages.

As used herein, the term "hard package" or the like includes packaging having a compartment with one or more openings that can be covered to create a seal. In one or more embodiments, the hard package includes one or more components made of a rigid material such as a rigid polymeric material. Examples of rigid polymeric materials include, but are not limited to, polyester, polycarbonate, polyethylene, polystyrene or polypropylene, or combinations or co-polymers thereof. In one or more embodiments, a hard package can thermoformed or molded, such as by injection molding.

As used herein, the term "microorganism" refers to a microbe or organism that is unicellular or lives in a colony of cellular organisms. Microorganisms are very diverse; they include, but are not limited to bacteria, fungi, archaea, and protozoans.

As used herein, the term "sterilization" refers to a means of eliminating or killing microorganisms present on a surface, contained in a fluid or in a compound such as biological culture media in order to achieve asepsis or a sterile microbial environment. Sterilization can be achieved by applying heat, chemicals, irradiation/radiation, high pressure, filtration, or combinations thereof. Chemical sterilization includes sterilization with gases such as ethylene oxide, hydrogen peroxide gas, and ozone, liquids such as chlorine bleach, iodine, glutaraldehyde and formaldehyde, ortho-phthaladehyde (OPA), hydrogen peroxide, peracetic acid, sodium hydroxide, silver, and cobalt. Radiation sterilization involves the use of radiation such as electron beams (E-beam), x-rays, gamma rays, or subatomic particles.

One or more embodiments of the present disclosure relates to a packaging system having a single compartment having a hard package which serves to protect a medical device, maintains sterility of the medical device and may also prevent undesired activation of a safety feature of the medical device prior to its intended use.

Figure 2:
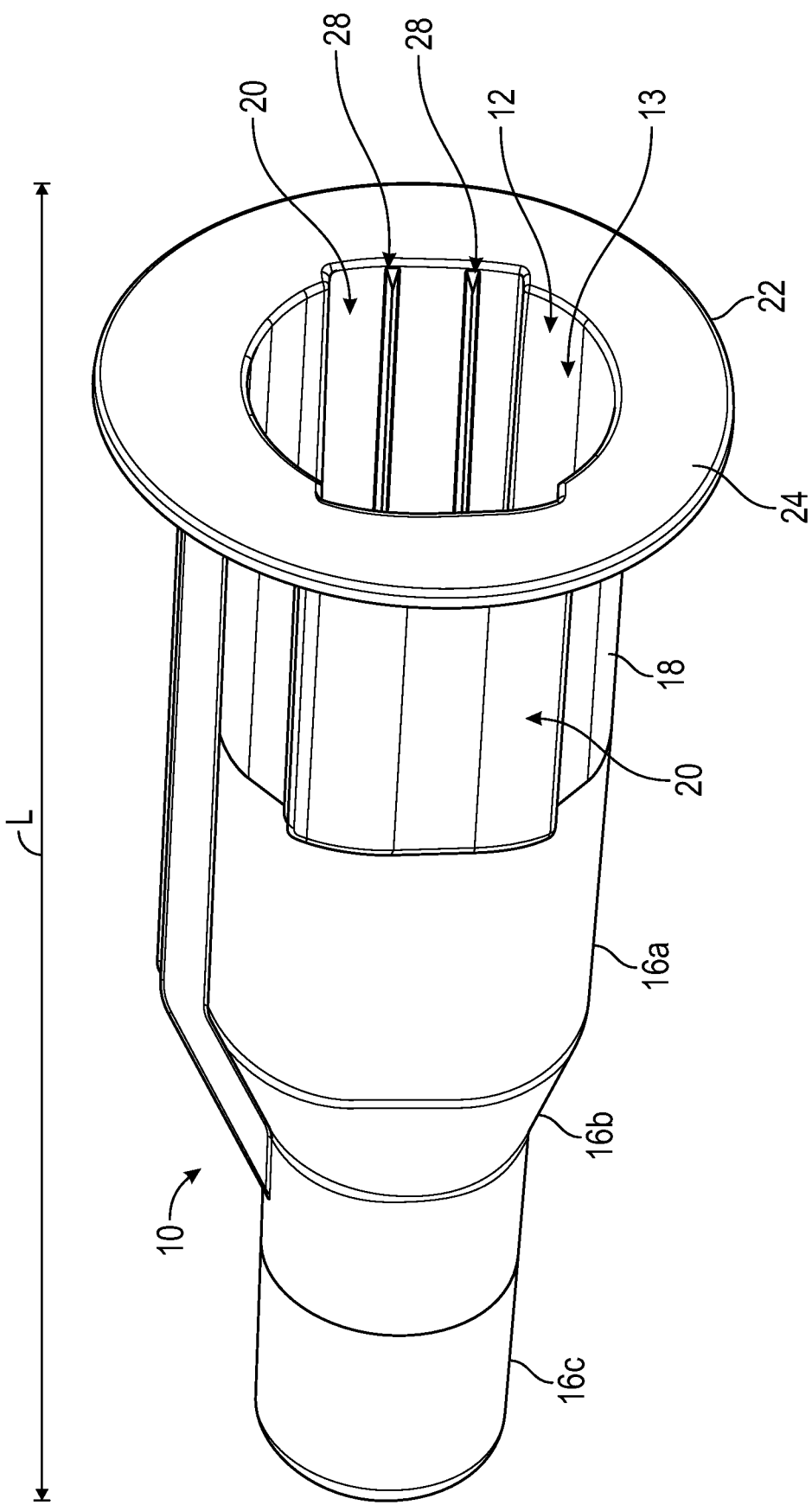
FIG. 2 illustrates a side view of the packaging of FIG. 1 having a cavity in a compartment of the packaging to nest a portion of a safety needle device.

FIGS. 1-4 illustrate an exemplary embodiment of a single compartment packaging 10 of the present disclosure. As shown in FIGS. 1 and 2, the single compartment package 10 may include an open proximal end 12, a closed distal end 14, a compartment 16 having a sidewall 18 extending between the closed distal end 14 and the open proximal end 12, one or more cavity 20 projecting outwardly from the sidewall 18 extending to the open proximal end 12, and a flange 22 disposed at open proximal end 12. The one or more cavities may be shaped to match the shape of a corresponding feature or element of a safety needle device. In one or more embodiments as shown in FIG. 2, the cavity may be rectangle-shaped.

As shown in FIG. 2, in one or more embodiments, the compartment 16 may include a first segment 16a, a second tapered segment 16b, and a third narrowed segment 16c.

As shown in FIG. 2, in one or more embodiments, one or more cavity 20 projects outwardly from sidewall 18 extending from the opening 13 of the open proximal end 12 in a distal direction along a portion or along the entirety of the length of compartment 16. In one or more embodiments, one or more cavity 20 projects outwardly from sidewall 18 extending from the opening 13 of the open proximal end 12 in a distal direction along a portion or along the entirety of the length of first segment 16a of compartment 16. In one or more embodiments, the one or more cavity 20 may be disposed 1-360° apart. In one or more embodiments, as shown in FIG. 2, the one or more cavity 20 may be disposed 180° apart. The cavity 20 extends radially outward relative to the longitudinal axis of the packaging 10. The cavity 20 also extends along at least a portion of the longitudinal length of the packaging 10. The cavity 20 is shaped such that the sidewall 18 bulges radially outward in the area of the cavity 20.

In one or more embodiments, as shown in FIG. 2, the inside surface 21 of compartment 16 includes a plurality of interference ribs 28. In one or more embodiments, the plurality of interference ribs 28 extends in a direction substantially parallel to the longitudinal axis "L" of the packaging 10. In one or more embodiments, plurality of interference ribs 28 may have any desired shape, including, but not limited to, triangular, square, rectangular, rounded, etc. In the embodiment shown in FIG. 2, the plurality of interference ribs 28 has a triangular shape. In one or more embodiments, the plurality of interference ribs are disposed on an inside surface of compartment 16. In one or more embodiments, the plurality of interference ribs are disposed on an inside surface at the distal end of the compartment 16. In one or more embodiments, the plurality of interference ribs 28 disposed on an inside surface at the distal end of the compartment 16 may center a safety needle device such that the safety needle device is coaxial to the package and thus prevents the safety needle device from shifting away from the activation prevention element. In one or more embodiments, the plurality of interference ribs are disposed on an inside surface at the proximal end of the compartment 16 and prevent or slow down axial travel of the safety needle device in the proximal direction, thus keeping the activation prevention element engaged with an activation element in the axial direction to prevent premature activation of the safety needle device when the device is nested in the package. In one or more embodiments, the plurality of interference ribs disposed on an inside surface at the proximal end of the compartment 16. In one or more embodiments, the plurality of interference ribs are disposed on an inside surface of the compartment 16 and do not extend to the proximal end of the compartment to for a lead in face such that a safety needle device 30 is centered with the compartment 16 or cavity 20 of the package 10 before interference is created when the safety needle device 30 is pushed distally into the package and makes contact with a plurality of interference ribs disposed on an inside surface at the distal end of the compartment 16.

Figure 3:
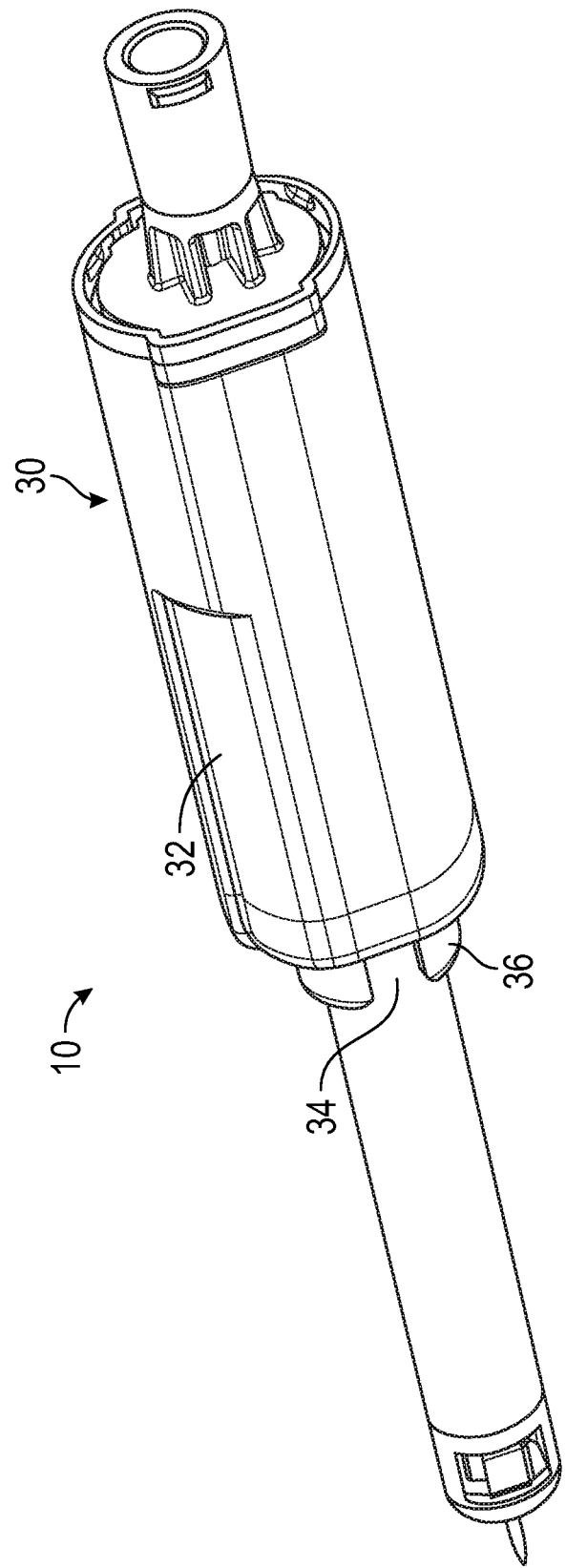
FIG. 3 illustrates a perspective view of a safety needle device that may be used with packaging according to one aspect of the present disclosure.
Figure 4:
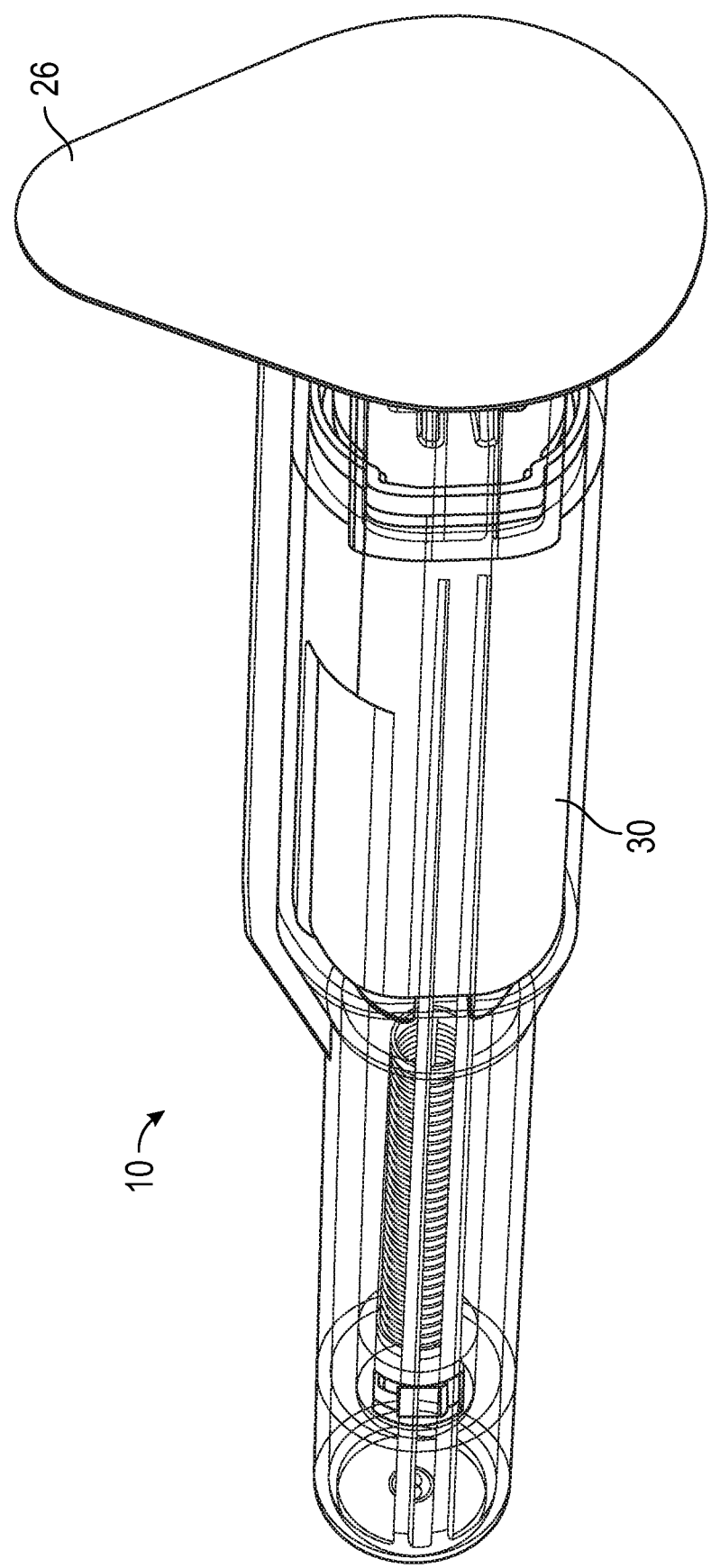
FIG. 4 illustrates a perspective view of a safety needle device placed within packaging according to one aspect of the present disclosure.
Figure 5:
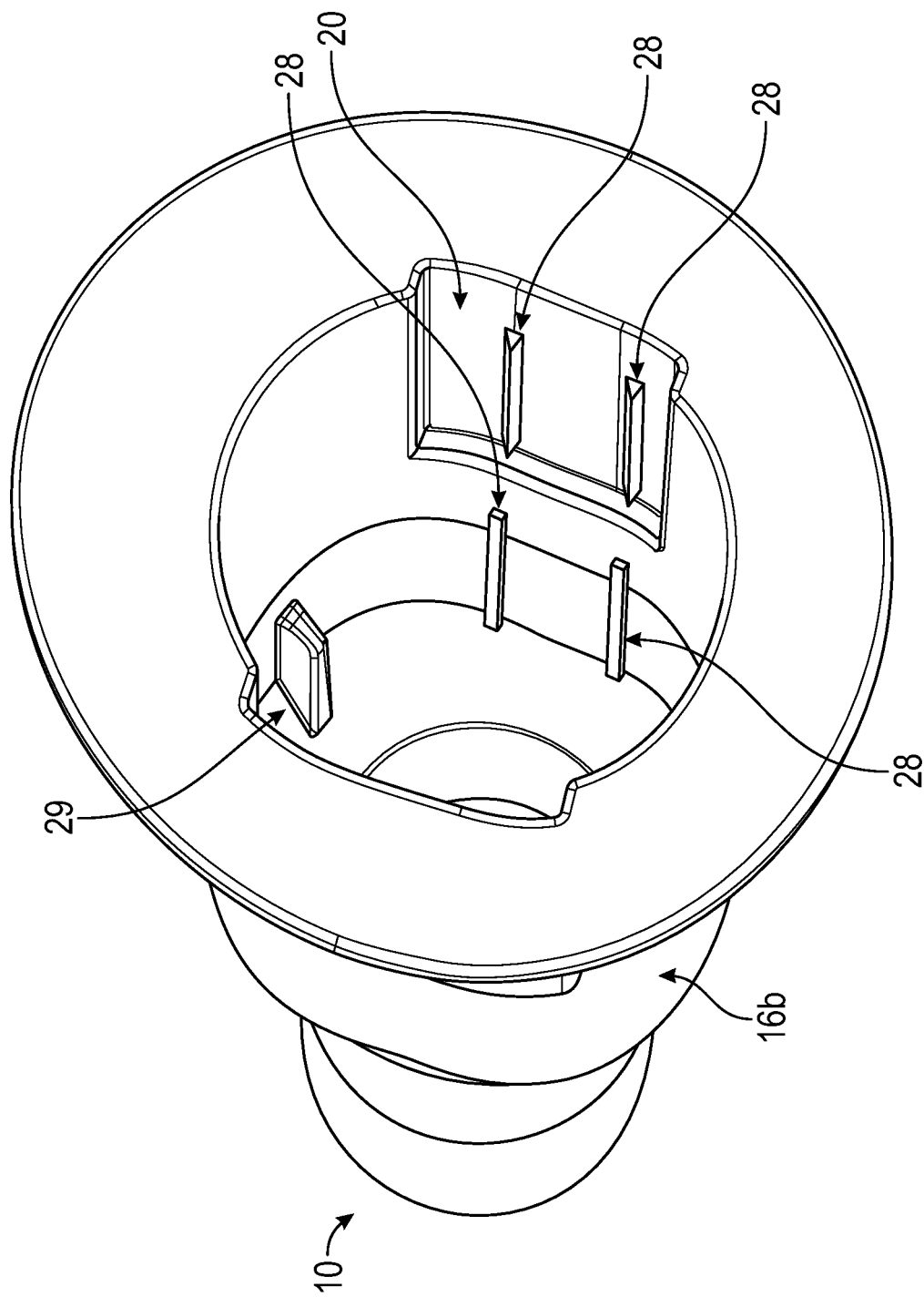
FIG. 5 illustrates a back right side view of the packaging of FIG. 2 having a cavity in a compartment of the packaging to nest a portion of a safety needle device.

FIG. 3 is a perspective view of a safety needle device 30 that can be used with embodiments of the packaging 10 of the present disclosure. FIG. 4 is a perspective view of a safety needle device 30 that can be used with embodiments of the packaging 10 of the present disclosure. The packaging 10 of the present disclosure can also be used with other suitable types of fluid transfer devices. In one or more embodiments, the packaging 10 may be made from a transparent or semi-transparent material. As shown in FIGS. 2 and 5, in one more embodiments, the face 24 of the flange 22 is a flat surface that interacts with a removable seal 26 disposed against the open proximal end 12. In an alternate embodiment, the flange 22 may have a raised edge with a recess in the flange. In one or more embodiments, the flange may have at least one flat edge. In one or more embodiments, removable seal 26 can act as a stop to limit the axial travel of the safety needle device 30 in the compartment 16.

In one or more embodiments, a clearance exists between the removable seal 26 and proximal segment of safety needle device 30 when the safety needle device 30 is fully positioned in the package 10. Compartment 16 and removable seal 26 define a sealed region in which the safety needle device 30 is disposed. In one or more embodiments, removable seal 26 can be a pull tab. The removable seal 26 can include a pull tab for a user to grab in order to remove the removable seal 26 to access the compartment 16.

In one or more embodiments, the removable seal 26 can include graphics, symbols, diagrams, words or other instructions. In one or more embodiments, the removable seal 26 may also include graphics, symbols, diagrams, words or other instructions to indicate the intended use of the needle stored in compartment 16.

Figure 6:
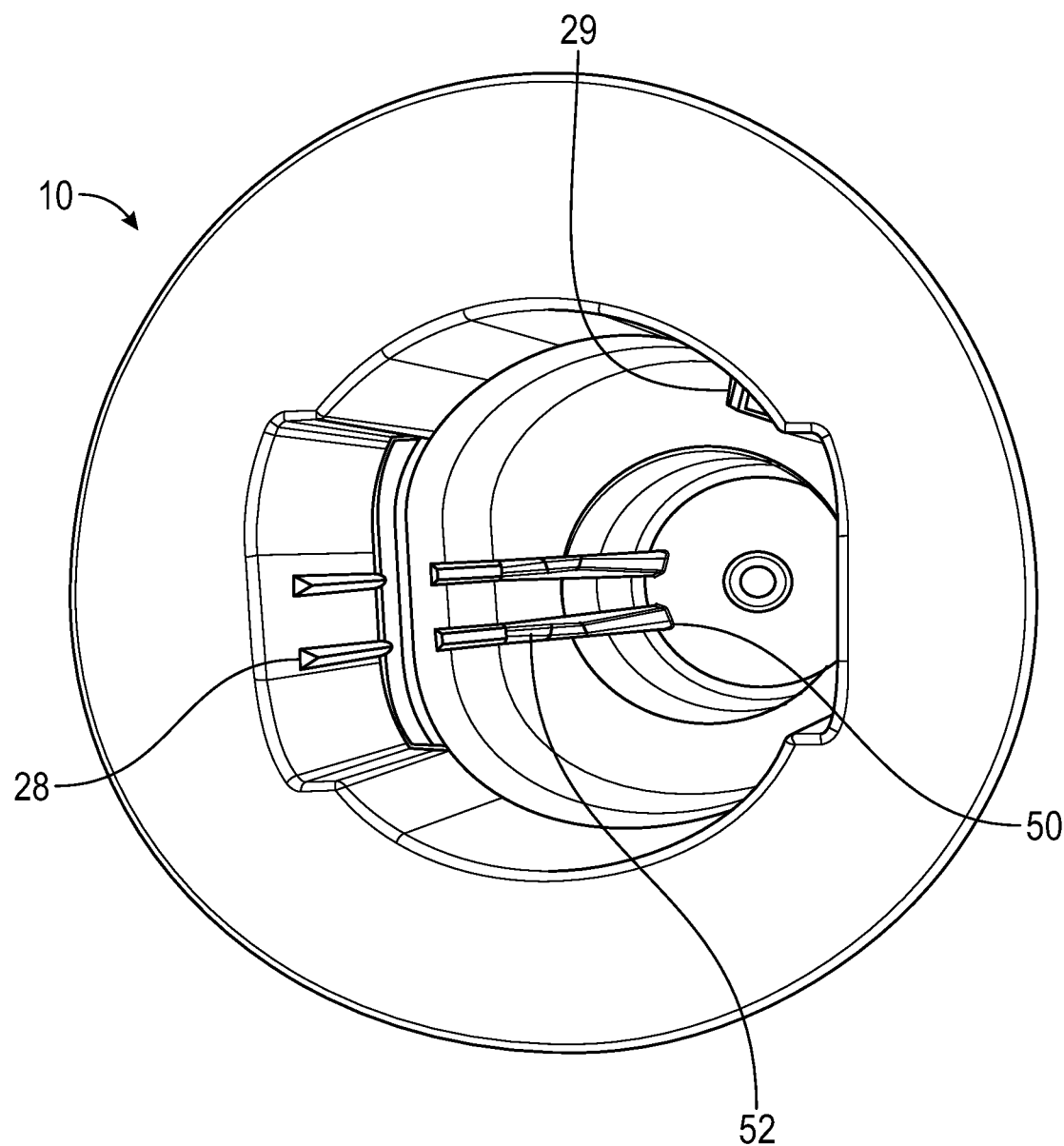
FIG. 6 illustrates a illustrates a back left side view of the packaging of FIG. 2 having a cavity in a compartment of the packaging to nest a portion of a safety needle device.

In one or more embodiments, as shown in FIGS. 5 and 6, the plurality of interference ribs 28 are separated equally about the circumference of the inside surface 21 of cavity 20 of packaging 10. In one or more embodiments, the plurality of interference ribs 28 may be oriented 1-360° apart around a circumference of the inside surface 21 of cavity 20 of packaging 10. In one or more embodiments, the plurality of interference ribs 28 may be oriented 180° apart. In another embodiment, the plurality of interference ribs 28 may be provided with equal or unequal separation about the circumference of the inside surface 21 of cavity 20. In one or more embodiments, as shown in FIG. 5, the plurality of interference ribs 28 is arranged in sets of two or more individual ribs. In one or more embodiments, the plurality of interference ribs 28 or one or more sets of interference ribs 28 are disposed 180° apart from each other.

Figure 17:
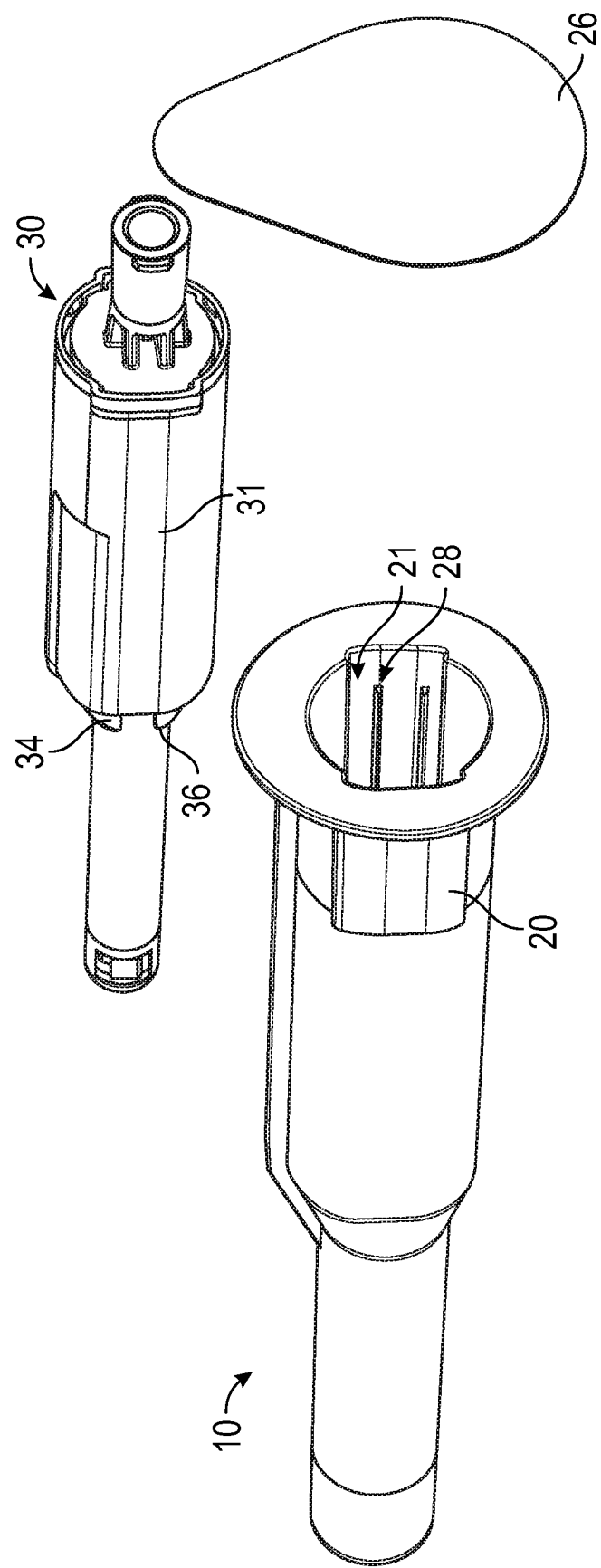
FIG. 17 illustrates an exploded view of the package according to one aspect of the present disclosure, a safety needle device and the resealable seal.

In one or more embodiments, as shown in FIG. 17, the interference ribs 28 disposed on the inside surface 21 of compartment 16 or cavity 20 are configured to engage a portion of the body 31 of a safety needle device 30 such that the safety needle device 30 is nested in the compartment 16 or cavity 20. In one or more embodiments, spacing of the interference ribs 28 on one side of the compartment 16 or cavity 20 is different than the spacing on the opposite side of the compartment 16 or cavity 20. In one or more specific embodiments comprising four (4) interference ribs, the spacing of two (2) interference ribs 28 on one side of the compartment 16 or cavity 20 is different than the spacing of the two (2) interference ribs 28 on the opposite side of the compartment 16 or cavity 20 creating a trapezoid-shaped structure to prevent any tilting of the safety needle device 30 when placed inside the compartment 16 or cavity 20. In one or more embodiments, the plurality of interference ribs 28 are configured to prevent movement of the safety needle device 30 within the compartment 16 or cavity 20 until a user purposefully removes the safety needle device 30 from the packaging 10. In particular, the plurality of interference ribs 28 may prevent the safety needle device 30 from sliding axially within the packaging 10, which can cause damage and wear to the safety needle device 30 or to the packaging 10. In one or more embodiments, interference ribs 28 extend proximally past the edge of an inserted safety needle device 30 such that the segment of the interference ribs 28 in contact with the safety needle device 30 yields, and the segment of the interference ribs 28 not in contact with the safety needle device 30 does not yield, thereby forming a detent that improves axial retention of the safety needle device 30 within the package 10.

In one or more embodiments, interference ribs 28 are disposed along a portion or the entire length of the inner surface of the compartment 16 of package 10. The interference ribs provide for a friction fit with safety needle device 30 that restricts movement of the safety needle device 30 within the packaging 10 and also acts to prevent the safety needle device 30 from falling out of package 10. The interference ribs also assist to align the safety needle device 30 in a left to right orientation. In one or more embodiments, interference ribs 28 are made from a polymeric material, including but not limited to, polyester, polycarbonate, polyethylene, polystyrene or polypropylene, or combinations or co-polymers thereof. In one or more embodiments, interference ribs 28 are initially engaged with a distal portion of the exterior surface of safety needle device 30 via friction fit to minimize rattling of safety needle device 30 when positioned in packaging 10. In one or more embodiments, the material properties of the polymeric material cause the interference ribs 28 to relax or deform over time resulting in the formation of a detent over the top of safety needle device 30 to prevent rattling of safety needle device 30 when positioned in packaging 10. In one or more specific embodiments, the interference ribs are made of polypropylene.

In one or more embodiments, as shown in FIGS. 2, 5, 6, 14, and 15 interference ribs 28 are triangle-shaped ribs to allow for interference with a portion of a body of a safety needle device 30.

Figure 18:
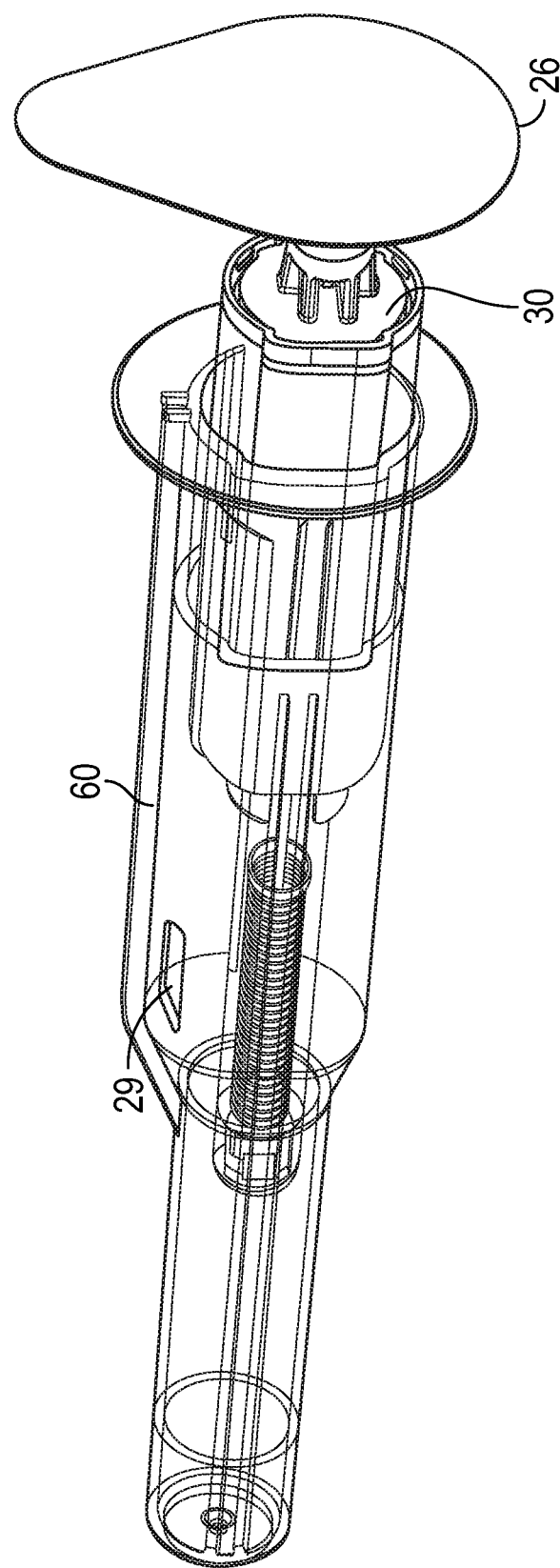
FIG. 18 illustrates a partially exploded view of the package according to one aspect of the present disclosure showing a safety needle device being inserted into the package and the resealable seal.

As shown in FIGS. 17 and 18, in one or more embodiments, the length of the interference ribs 28 extend beyond the body of the safety needle device 30 when the safety needle device 300 is positioned in packaging 10. The length of interference ribs 28 must be sufficient to provide enough friction between the package 10 and the safety needle device 30 because if user takes safety needle device 30 out of package 10 and then safety needle device 30 is rotated at an angle, e.g. 180° or any angle ranging from 1-360°, the safety needle device 30 will not go all the way into the package because safety needle device 30 is not perfectly symmetrical. Therefore, having the length of the interference ribs 28 extend beyond the body of the safety needle device 30 allows interference ribs 28 to extend far enough back increases the surface area for the friction caused by the interference ribs 28 against the body 31 of safety needle device 30 such that the safety needle device 30 will not fall out of the package 10. Therefore, if necessary, the user can remove the safety needle device 30 from the package 10 and can use the package 10 to re-cap or connect a second device to the safety needle device 30 if necessary because the interference ribs 28 grip the safety needle device 30 to prevent the safety needle device 30 from falling out of the package 10. In one or more embodiments, interference ribs 28 run to the open proximal end 12 of package 10 to mitigate against the plastic material relaxing to form only a detent as stress in the plastic material of the interference rib 28 relax to form a detent over time to cover the safety needle device 30.

Figure 19B:
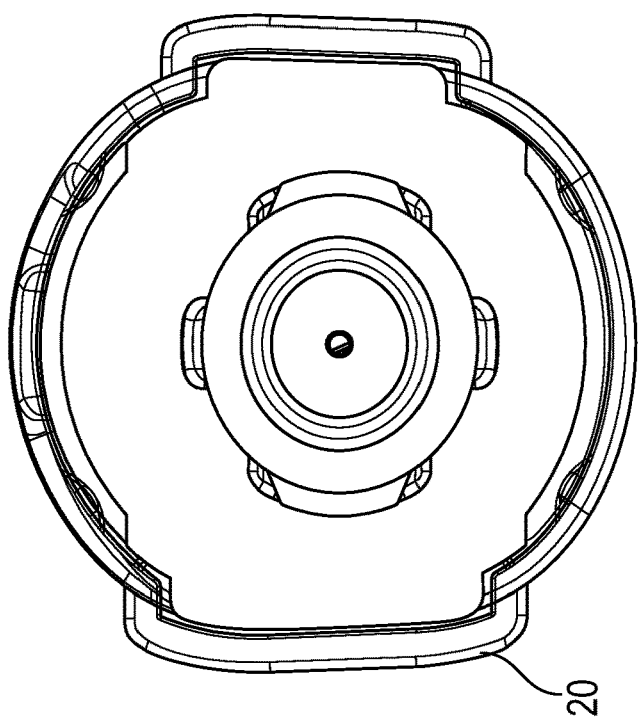
FIG. 19B illustrates a front view of the package according to one aspect of the present disclosure showing a safety needle device inserted into the package.
Figure 19A:
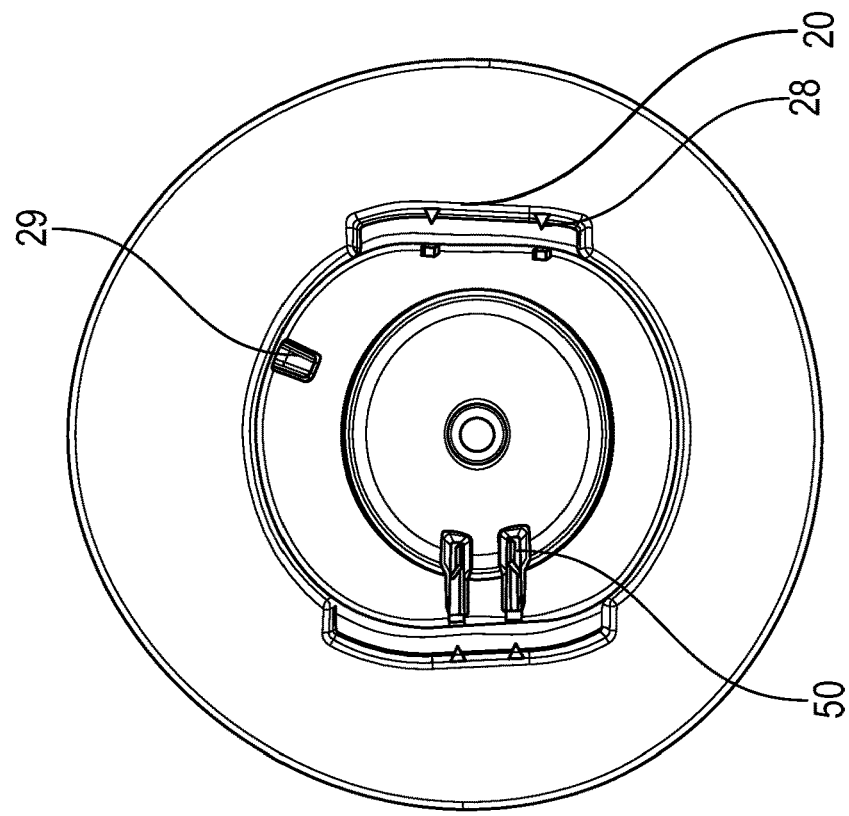
FIG. 19A illustrates a back view of the package according to one aspect of the present disclosure showing a safety needle device inserted into the package.

FIG. 18 illustrates a partially exploded view of the package according to one aspect of the present disclosure showing a safety needle device being inserted into the package and the resealable seal;

FIGS. 19A and 19B illustrates a back and front view of the package according to one aspect of the present disclosure showing a safety needle device inserted into the package.

Figure 20:
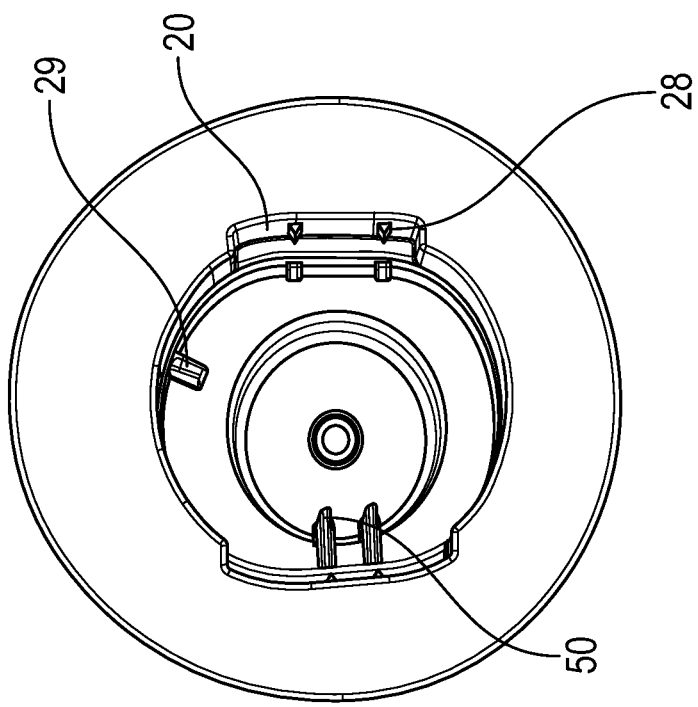
FIG. 20 illustrates a perspective view of the alignment of an off-centered short rib of package and the corresponding detent on the exterior surface of a safety needle device prior to being placed within packaging according to one aspect of the present disclosure.
Figure 20:
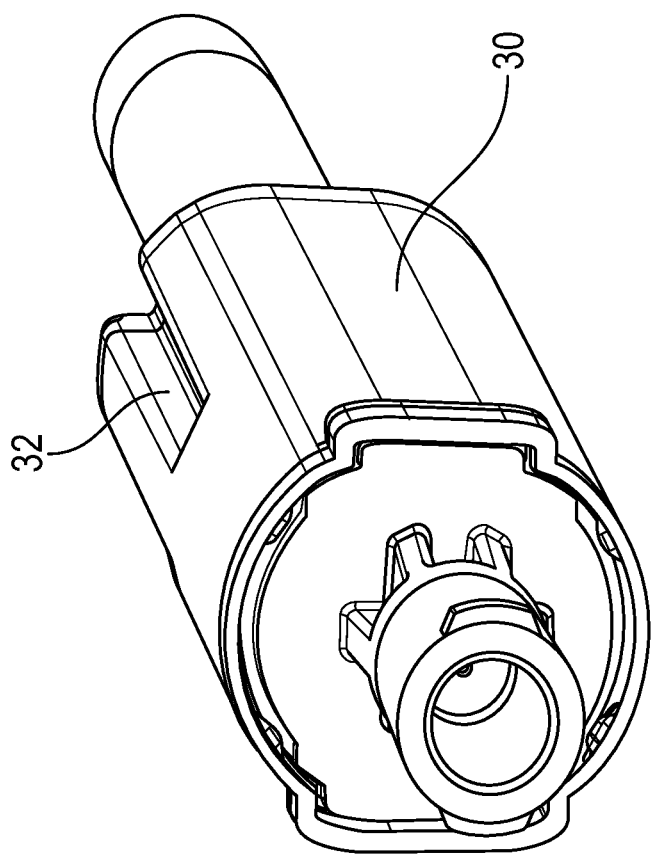

In a specific embodiment, as shown in FIGS. 17-20, cavity 20 is shaped to nest a protruding segment of a body 31 of safety needle device 30. In one or more embodiments, the one or more sets of interference ribs 28 may be spaced close together or spaced further apart from one another, as shown in FIG. 20. In one or more embodiments, the individual ribs comprising the one or more sets of interference ribs 28 may be spaced close together or spaced further apart from one another. In one or more embodiments, interference ribs 28 on one side of the inside surface 21 of the cavity 20 maybe spaced closer together in comparison to the interference ribs 28 on the opposite side of the inside surface 21 of the cavity 20 which are spread further apart. In one or more embodiments, the interference ribs 28 are spaced apart from each other.

In an alternate embodiment with a raised edge on the flange 22, the interference rib 28 run the entire length of the safety needle device 30.

In one or more embodiments, interference ribs 28 align safety needle device 30 in the package 10 from left to right orientation.

In one or more embodiments, as shown in FIG. 2, interference ribs 28 run along the entire length of the inside surface 21 of the compartment 16 of the package 10 from the open proximal end 12 to the closed distal end 14.

In one or more embodiments, safety needle device 30 that will be inserted into package 10 will not have a symmetrical structure. Thus, in one or more embodiments as shown in FIGS. 5 and 20, a short rib 29 extends in a proximal direction from the second tapered segment 16b of the compartment of the package 10 to ensures that the needle safety device is inserted in package 10 interacts with a corresponding slot 32 located on the exterior of housing of safety needle device 30.

As shown in FIGS. 5 and 20, in one or more embodiments, short rib 29 is disposed off-center to interact with corresponding slot 32 located on the exterior of housing of safety needle device 30.

In addition to accommodating a portion of the safety needle device 30, the short rib 29 also orients the safety needle device 30 such that it can be fully received in the compartment 16 of package 10 in one direction only. Other features of the safety needle device 30 or the packaging 10 may be also be used to align the safety needle device 30 within the compartment 16 of package 10. If safety needle device 30 is inserted incorrectly, short rib 29 will not be aligned with corresponding slot 32 located on the exterior of housing of safety needle device 30 thus preventing the safety needle device 30 from being fully inserted into the package 10.

In one or more embodiments, as shown in FIGS. 10-16, a notch or slot of a rotating feature of the safety needle device may interface with an anti-rotation feature of the packaging 10 to prevent activation or rotation of the safety needle device 30 relative to the packaging 10. In one or more embodiments, as shown in FIGS. 6, 19 and 20 activation prevention element 50 align the safety needle device 30 in a centered position in the package 10. In one or more embodiments, as shown in FIG. 17, activation prevention element 50 engage with a corresponding slot, notch or recess 34 located on the passive rotational activation element 36 of the safety needle device 30. In one or more embodiments, activation prevention element 50 may be disposed on the inside surface 21 of compartment 16 extending between the closed distal end 14 and the third narrowed segment 16c of compartment 16. Activation prevention element 50 make contact with the activation element 36 of safety needle device 30 such that the safety needle device 30 stays aligned relative to the package and therefore activation prevention element 50 remains engaged with slot, notch or recess 34 in the passive rotational activation element 36 of the safety needle device 30. In one or more embodiments, the activation prevention element 50 is in the form of ribs protruding outwardly into the cavity of compartment 16. In an alternate embodiment, a notch or slot of a packaging 10 may interface with an anti-rotation feature of the rotating feature of the safety needle device to prevent activation or rotation of the safety needle device 30 relative to the packaging 10. In one or more embodiments, activation prevention element on the device engage with a corresponding slot, notch or recess 34 located on the inside surface of the compartment 16 of the packaging. In one or more embodiments, activation prevention element 50 may be disposed on the inside surface 21 of compartment 16 or on the exterior surface of the safety needle device 30.

In an alternate embodiment, an activation prevention element of safety needle device may make contact with the activation element of the packaging such that the safety needle device stays aligned relative to the package and therefore activation prevention element of the safety needle device remains engaged with slot, notch or recess in the package. In one or more embodiments, the activation prevention element 50 is in the form of ribs protruding outwardly from the inside surface of the compartment 16 or protruding outwardly from the exterior surface of the safety needle device 30. In one or more embodiments, removable seal 26 can act as a stop to limit the axial travel of the safety needle device 30 in the compartment thereby maintaining the corresponding slot, notch or recess located on the package 10 to be engaged to the activation prevention element of a safety needle device.

Figure 9:
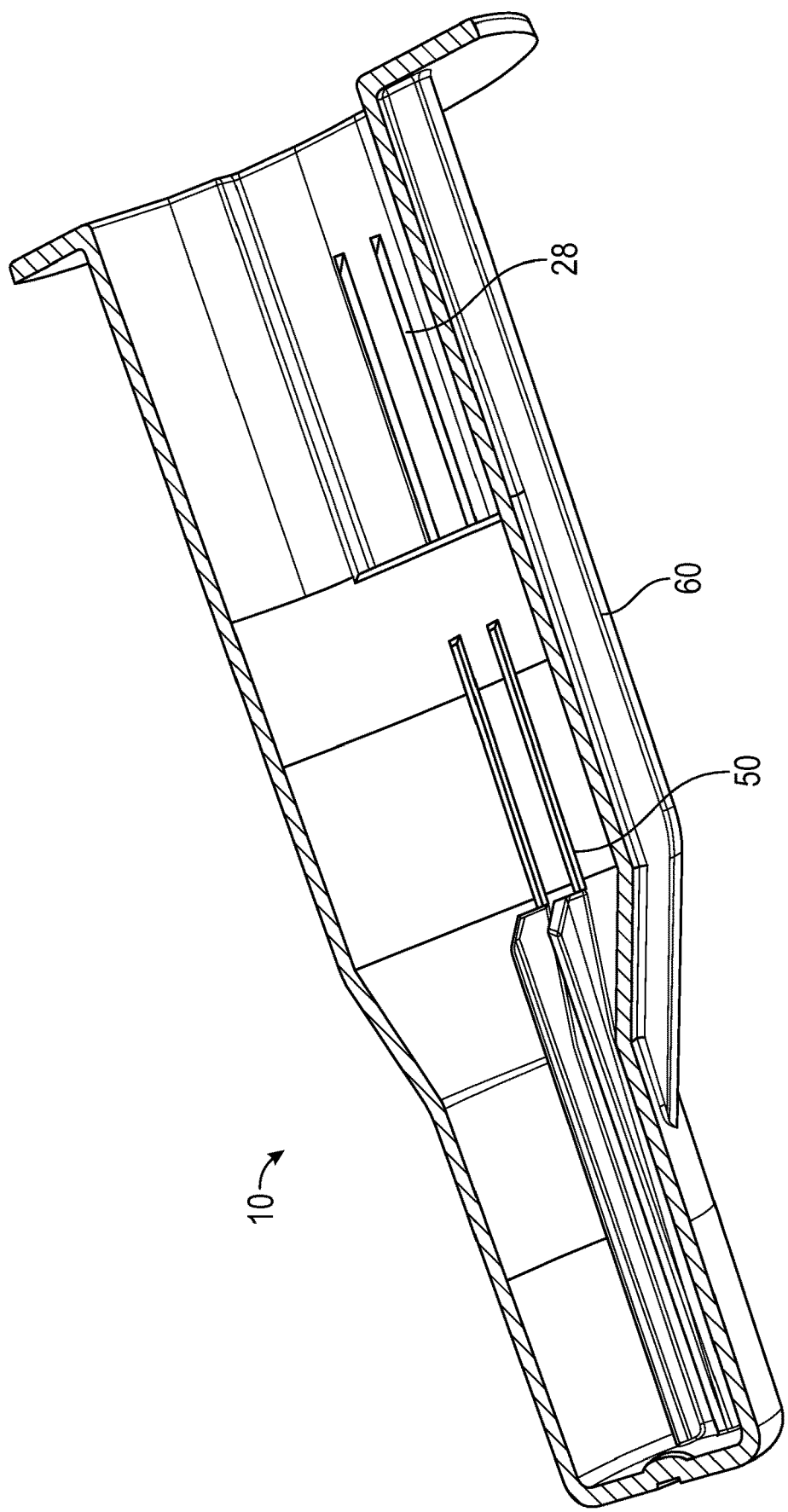
FIG. 9 illustrates a cross-sectional view of the packaging of FIG. 2 having an external rib and cavity in a compartment.
Figure 10:
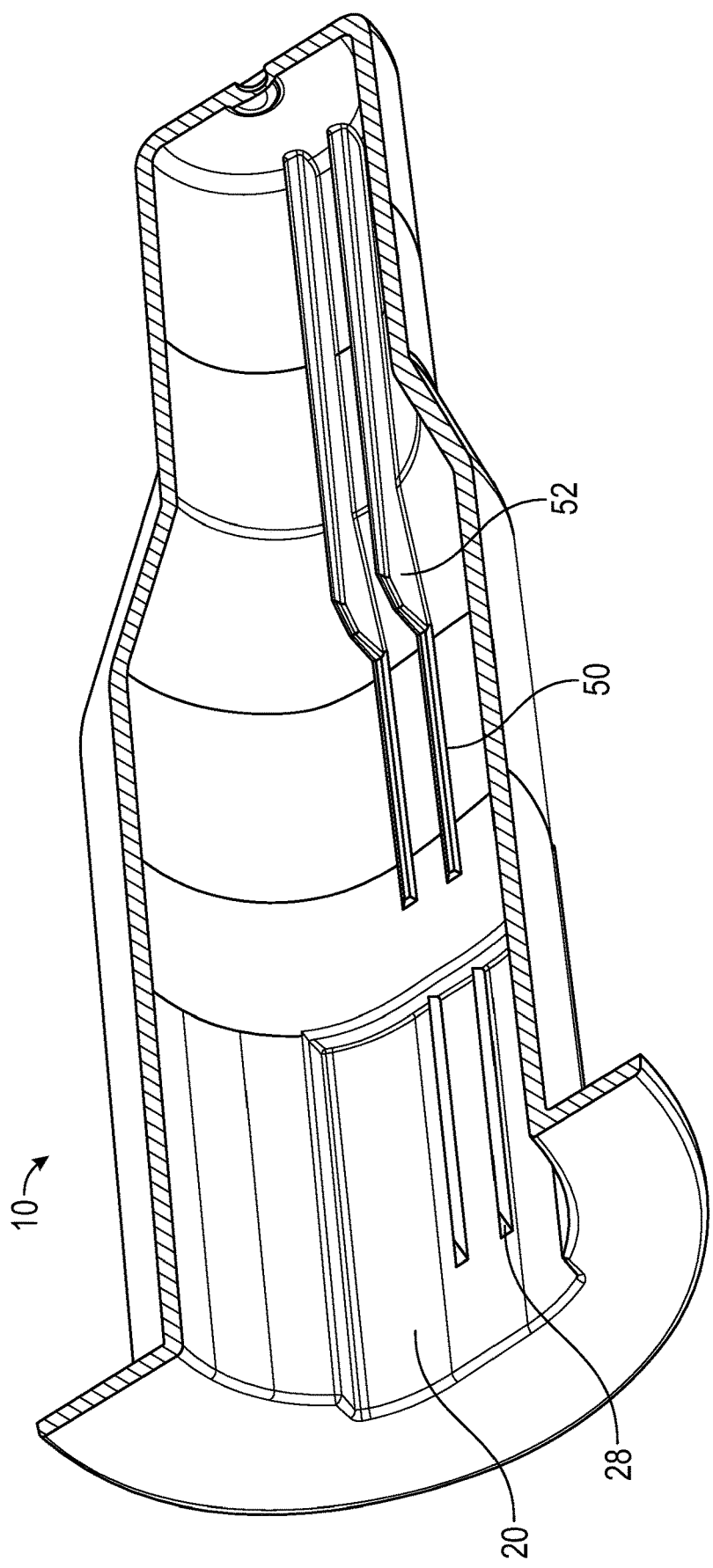
FIG. 10 illustrates another cross-sectional view of the packaging according to one aspect of the present disclosure having interference ribs and an activation prevention element.
Figure 11:
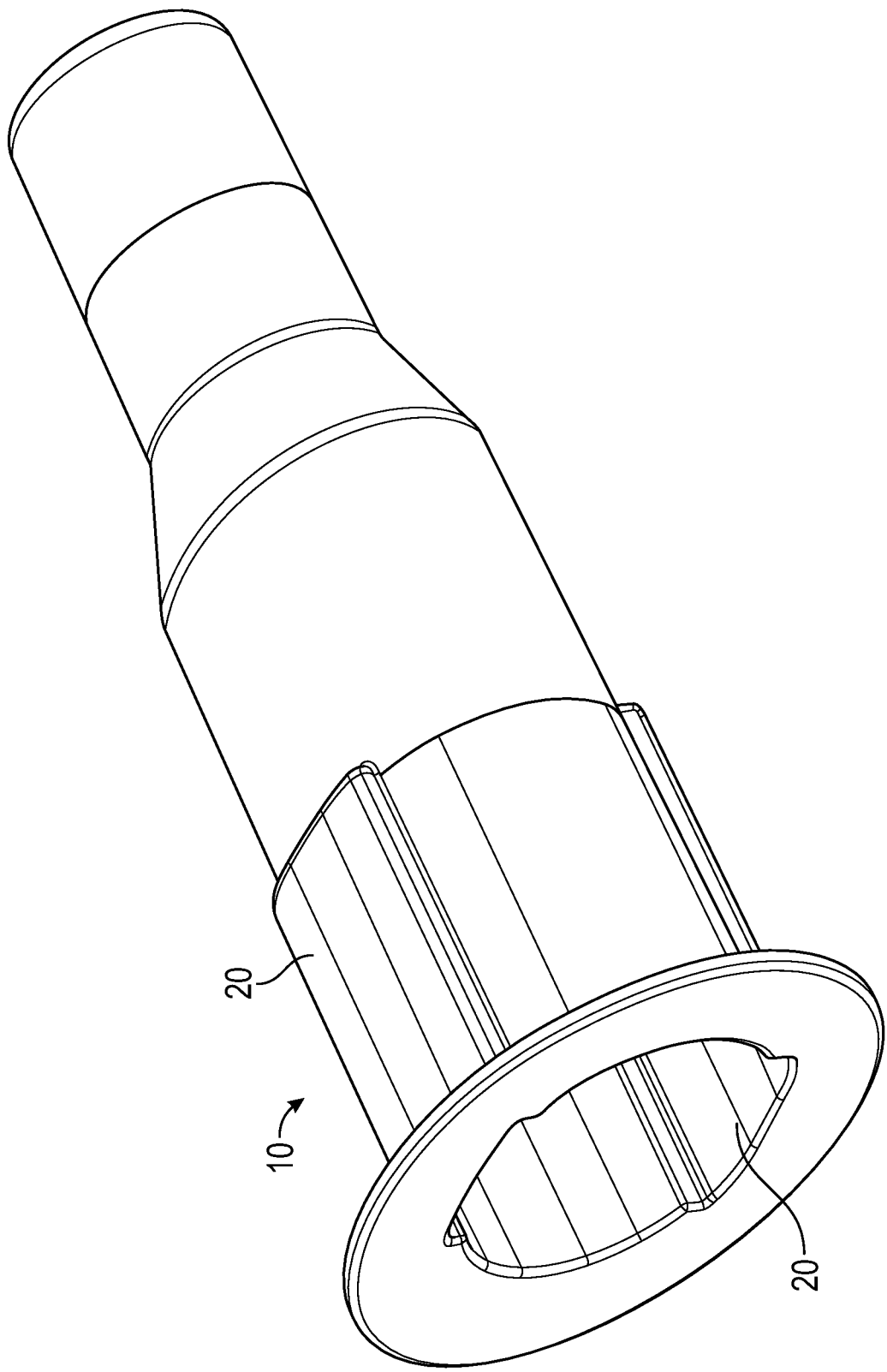
FIG. 11 illustrates a side view of the packaging according to one aspect of the present disclosure having a cavity in a compartment.
Figure 12:
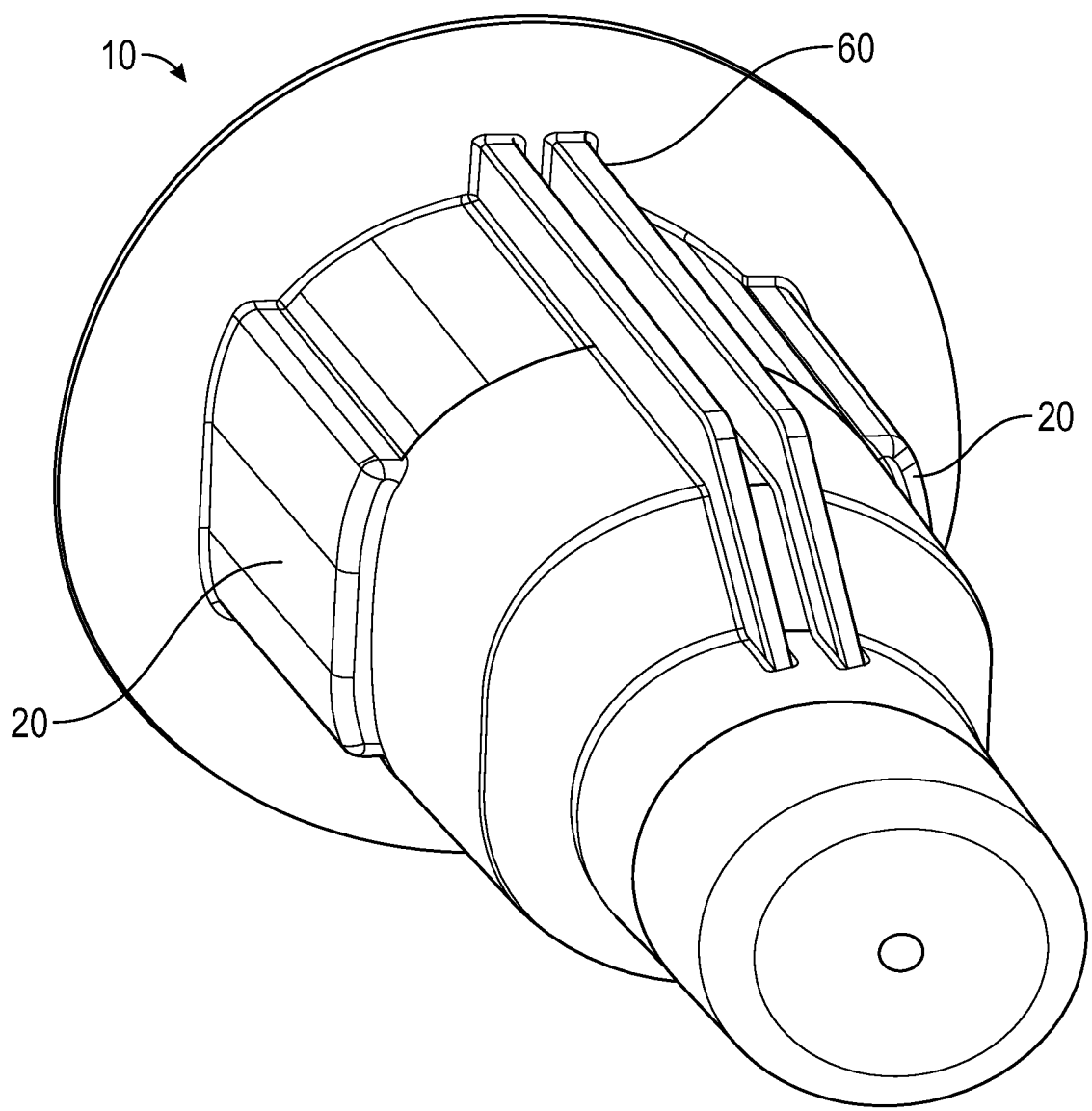
FIG. 12 illustrates a front view of the packaging according to one aspect of the present disclosure having a cavity in a compartment and an external rib.
Figure 13:
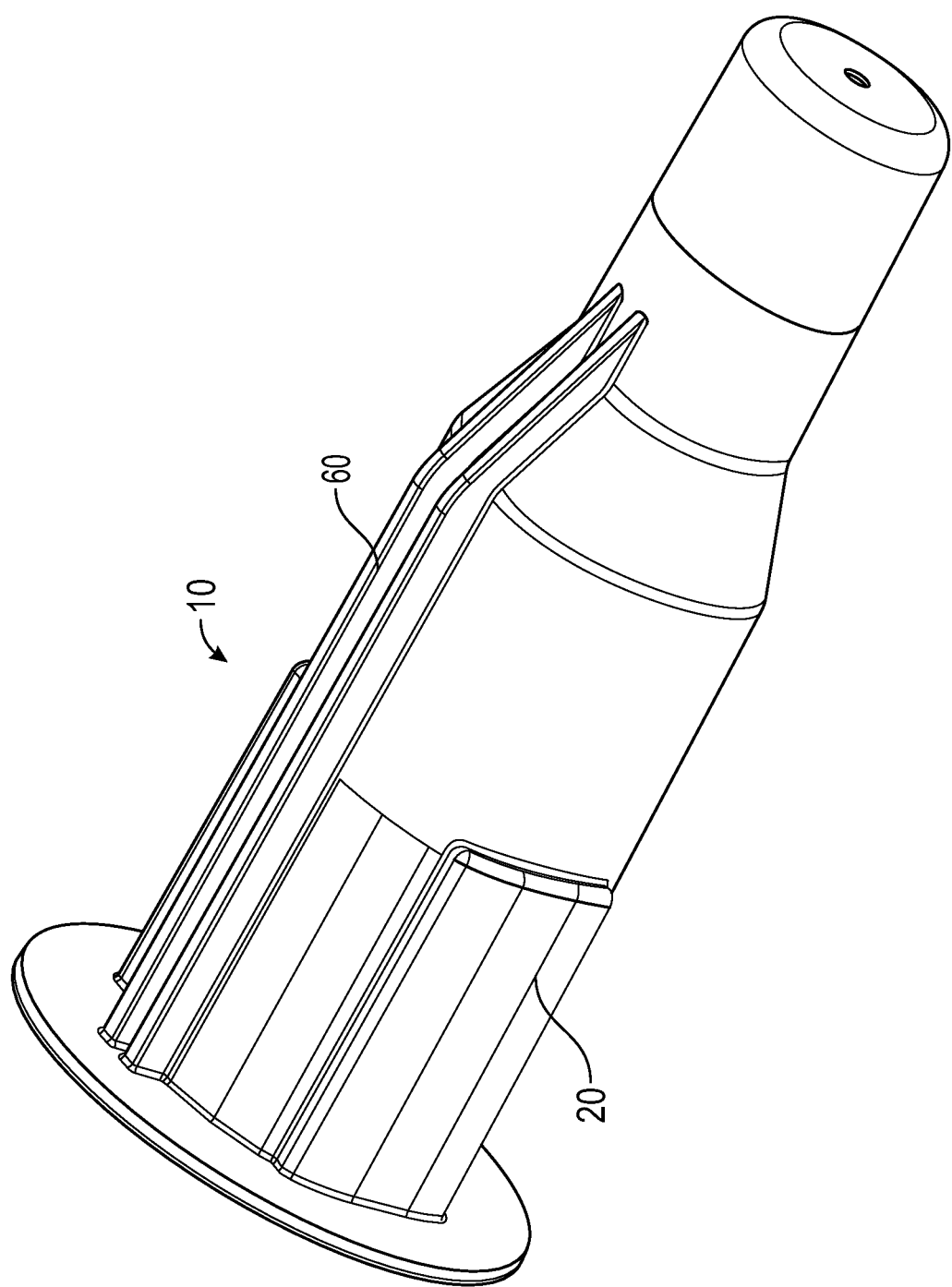
FIG. 13 illustrates a side view of the packaging according to one aspect of the present disclosure having a cavity in a compartment and an external rib.
Figure 14:
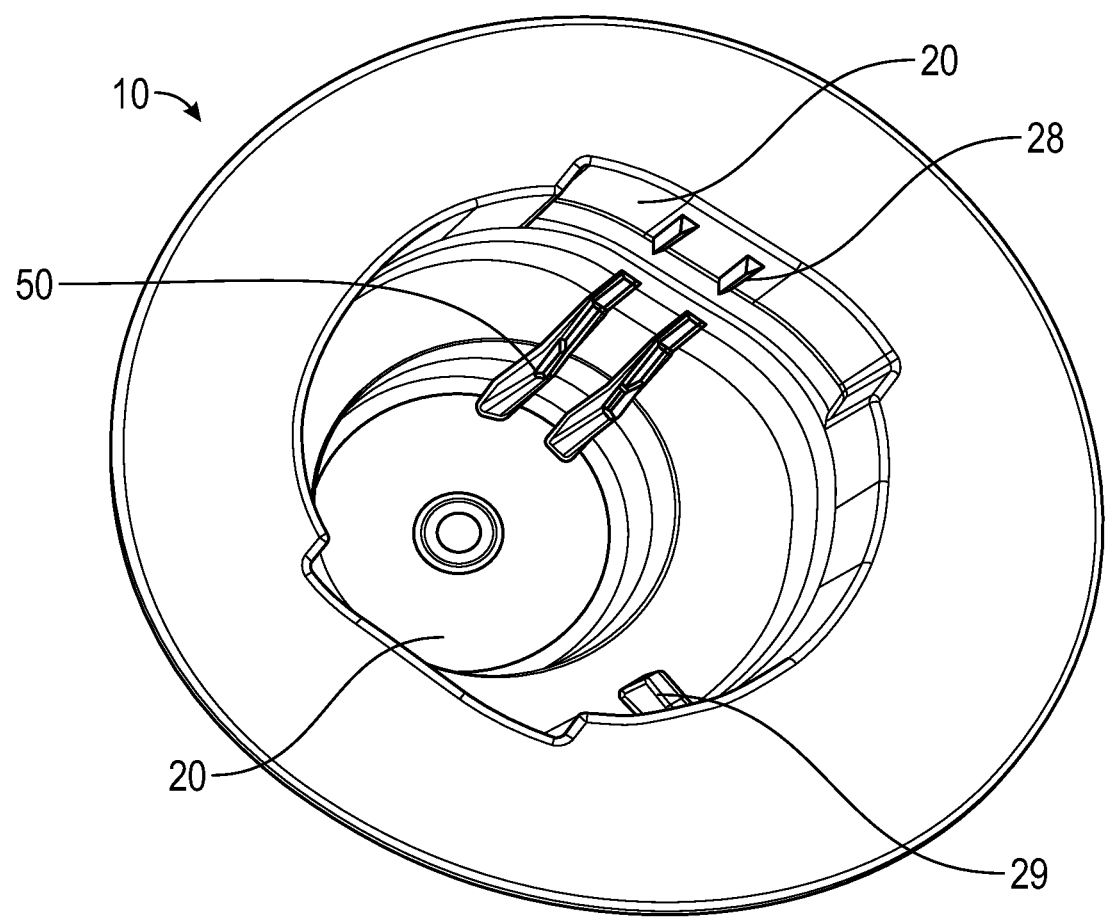
FIG. 14 illustrates a back view of the packaging according to one aspect of the present disclosure having a cavity in a compartment, interference ribs, short off-center alignment rib and an activation prevention element.
Figure 15:
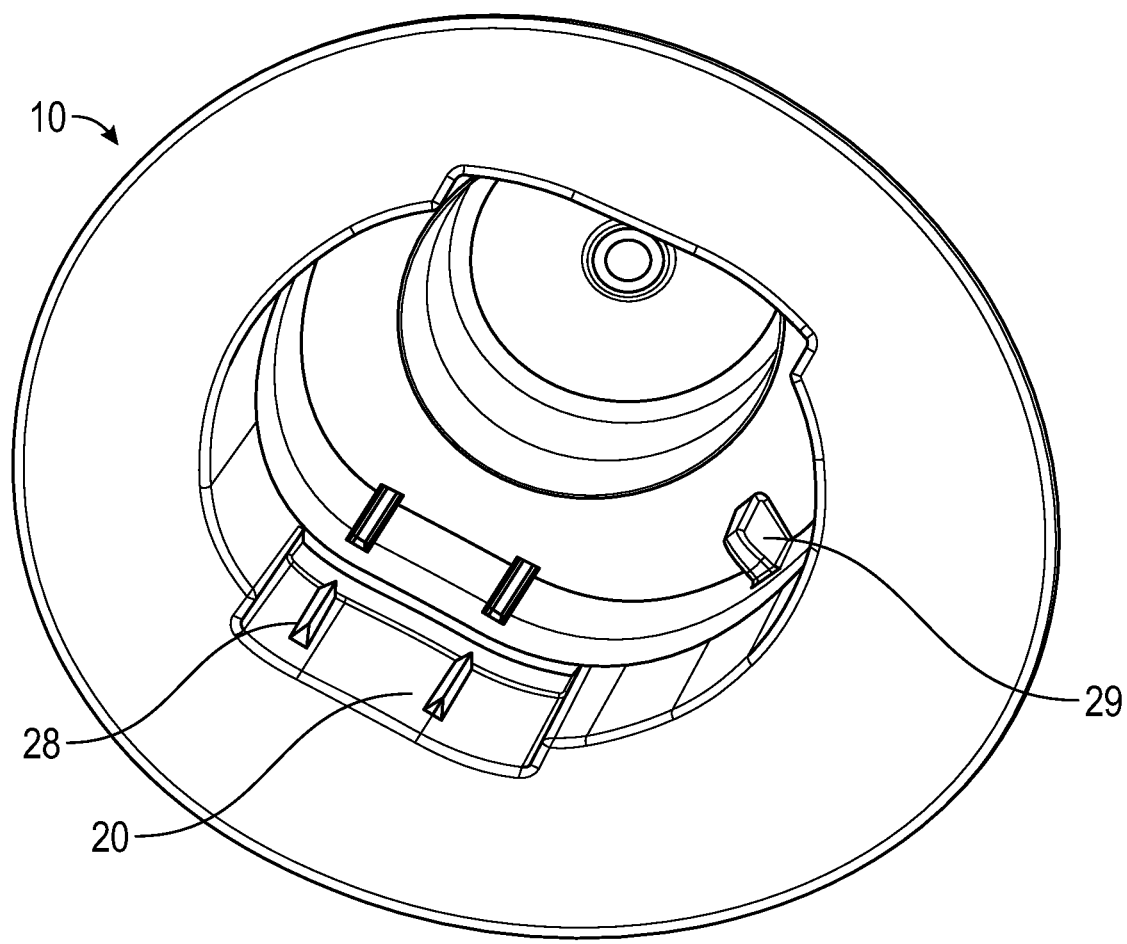
FIG. 15 illustrates another back view of the packaging according to one aspect of the present disclosure having a cavity in a compartment, interference ribs, short off-center alignment rib and an activation prevention element.
Figure 16:
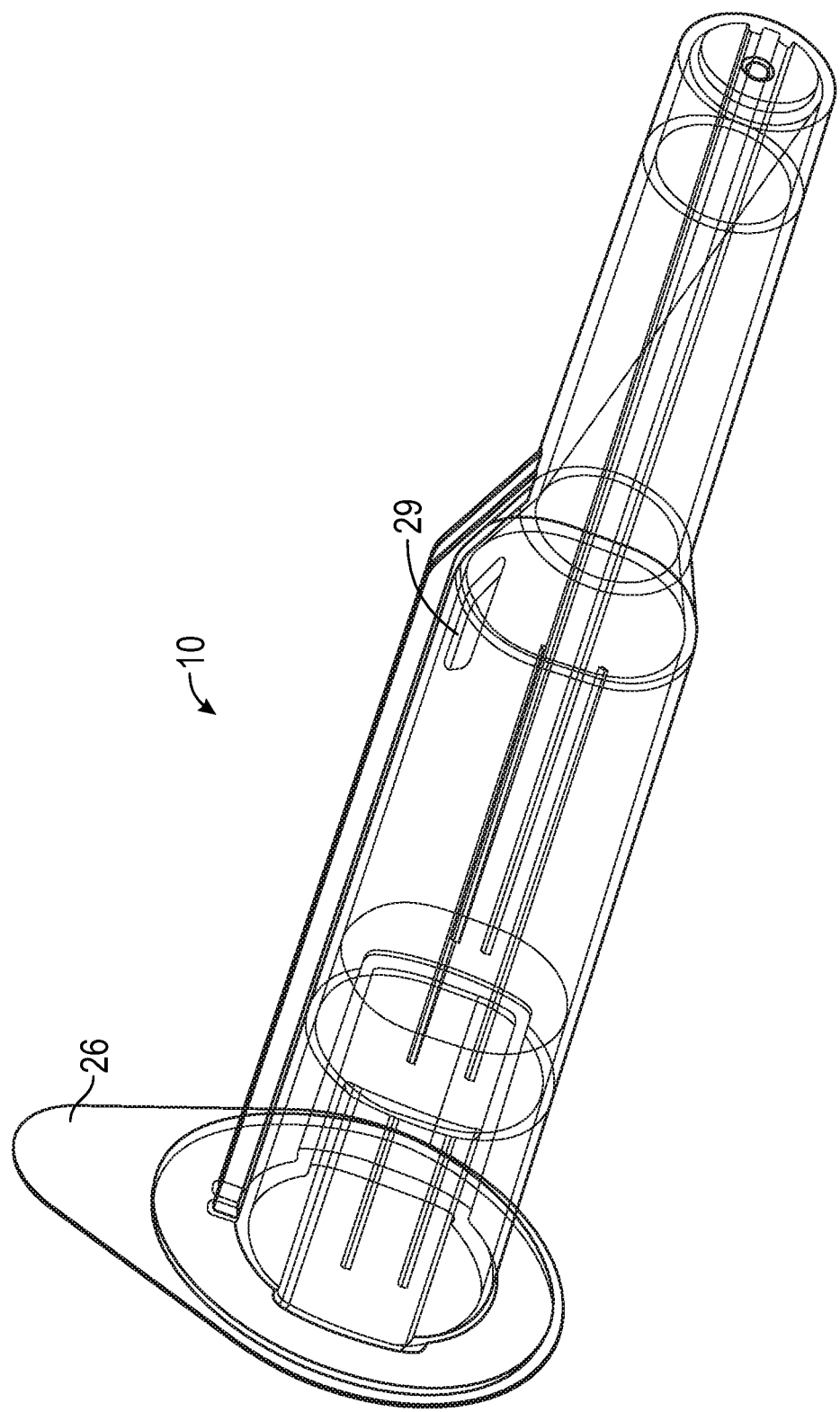
FIG. 16 illustrates a perspective view of a safety needle device placed within packaging according to one aspect of the present disclosure.

As shown in FIGS. 9 and 10, an activation prevention element 50 in the compartment 16 can nest the passive rotational activation element 36 of the safety needle device 30. In one or more embodiments, as shown in FIGS. 9 and 10, the activation prevention element 50 comprises one or more protrusions that extend inwardly into the compartment 16 and engages with a slot, notch or recess 34 in the passive rotational activation element 36 of the safety needle device 30 to prevent movement or rotation of the passive rotational activation element 36 of the safety needle device 30 prior to the intended use of the medical device by the user. In one or more embodiments, the passive rotational activation element 36 of the safety needle device 30 is a tether. In a specific embodiment, the passive rotational activation element 36 of the safety needle device 30 is a rotating tether. In a specific embodiment, the activation prevention element 50 interdigitates with a passive rotational activation element 36 of the safety needle device 30 in the form of a tether of the safety needle device 30. In a specific embodiment, activation prevention element 50 engages with a passive rotational activation element 36 of the safety needle device 30 in the form of a tether so that tether cannot rotate while device is inserted in the package 10.

In one or more embodiments, as shown in FIGS. 6-14, the activation prevention element 50 may include a tapered leading edge 52 that is configured to guide a portion of the safety needle device 30 into the packaging 10. In particular, the safety needle device 30 includes a corresponding slot, notch or recess 34 located on the passive rotational activation element 36 of the safety needle device 30 that are configured to receive the tapered leading edge 52 of the activation prevention element 50 to guide insertion of the safety needle device 30 into the packaging 10. The positioning of the tapered leading edge 52 of the activation prevention element 50 into the corresponding slot, notch or recess 34 located on the passive rotational activation element 36 of the safety needle device 30 restricts rotational movement of the safety needle device 30 relative to the packaging 10 to prevent wear and damage to the packaging 10 and safety needle device 30. In one or more embodiments, tapered leading edge 52 can be large enough to preload the safety opposite in rotation of activation to take up any manufacturing tolerance, and system flex or slack.

In one or more embodiments, the interference ribs 28 may be disposed in parallel to the activation prevention element 50.

In one or more embodiments, the interference ribs 28 align the safety needle device 30 from left to right in the compartment 16 to ensure that activation prevention element 50 properly engages with the corresponding slot, notch or recess 34 located on the passive rotational activation element 36 of the safety needle device 30 to ensure that safety needle device 30 cannot be inserted into package incorrectly.

In one or more embodiments, a clearance exists between the closed distal end 14 and a distal tip of a needle cannula of safety needle device 30 when the safety needle device 30 is fully positioned in the package 10.

Figure 7:
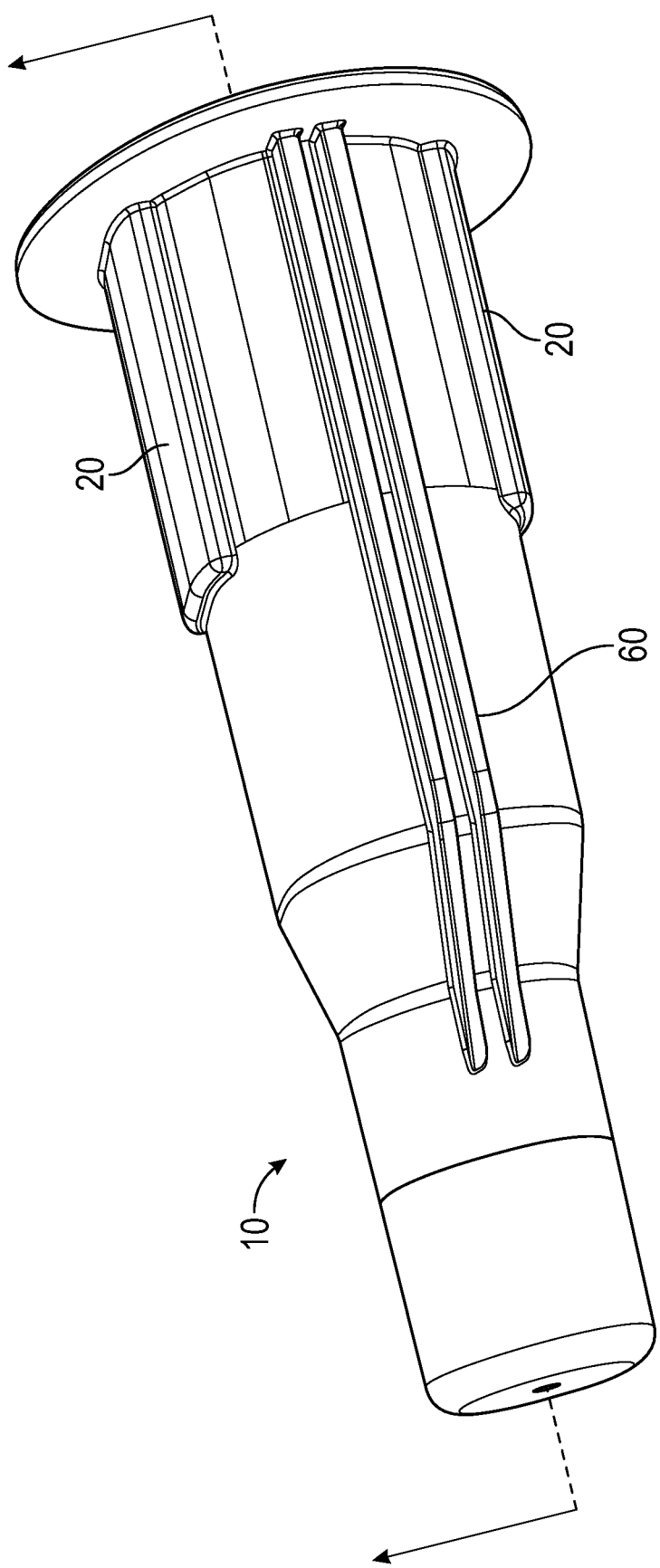
FIG. 7 illustrates a top view of the packaging of FIG. 2 having an external rib and cavity in a compartment of the packaging to nest a portion of a safety needle device.
Figure 8:
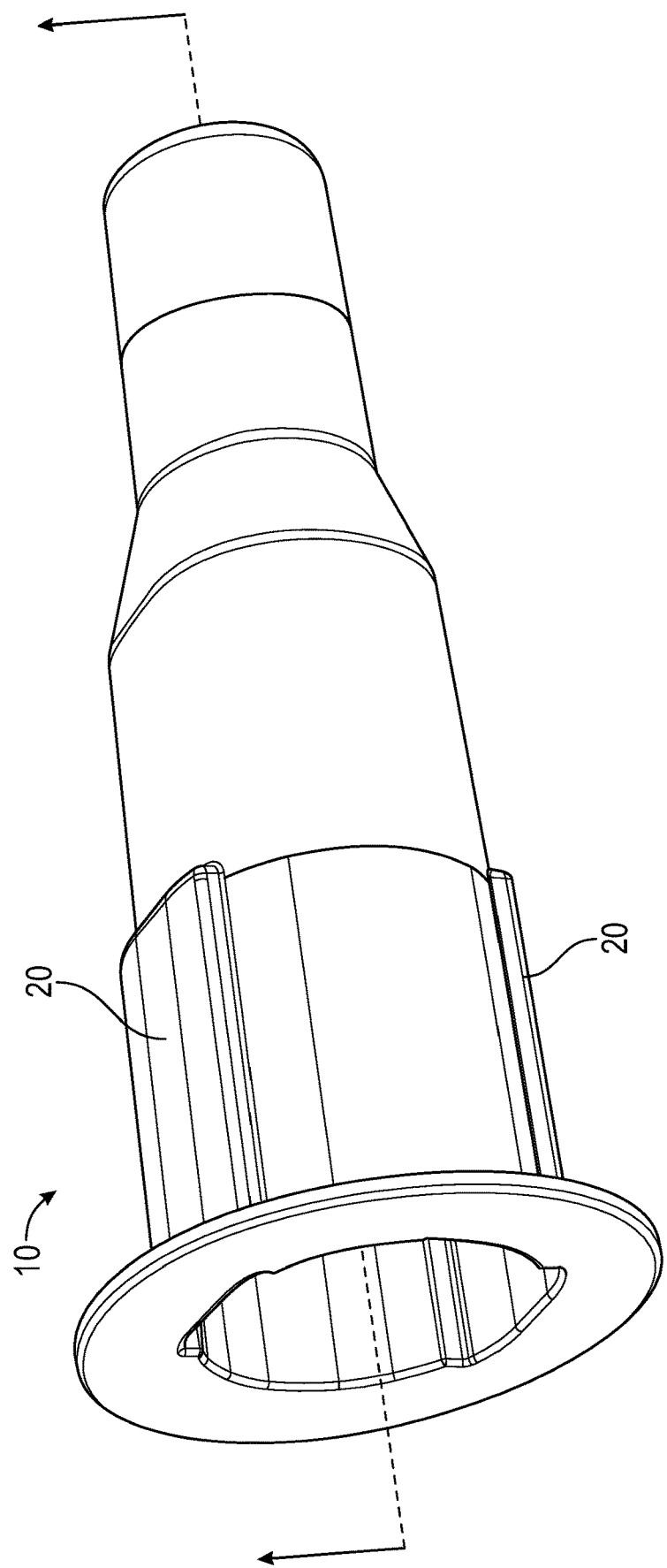
FIG. 8 illustrates a bottom view of the packaging of FIG. 2 having a cavity in a compartment.

As shown in FIGS. 7-9, in one or more embodiments, packaging 10 includes at least one external rib 60 that extend radially outward from the sidewall 18 of the packaging 10. In one or more embodiments, external rib 60 serves as a mating feature which allows for the nesting or attachment of a second hard pack. In one or more embodiments, the second hard pack may be a blunt fill cannula hard pack. In one or more embodiments, the blunt fill needle hard pack may be slidably attached to the external rib 60 of packaging 10. In one or more alternate embodiments, external rib 60 of package 10 may also be attached to the second hard package via press fitting, an adhesive bond, a solvent bond, a ring connector, heat shrink, shrink wrap, a snap fit, a C-clip snap, heat staking or ultrasonic welding. In one or more embodiments, the external ribs 60 of packaging 10 allow for discarding the second hard pack immediately after used.

As shown in FIGS. 1-9 and 11-20, the single compartment packaging 10 can be molded in a single piece, such as by injection molding. The packaging 10 may be constructed from any known material, such as a molded, injected, or thermo-formed plastic material. In one or more embodiments, the package is made of polypropylene.

In one or more embodiments, safety needle device 30 may be a passive safety needle or an active safety needle.

Various embodiments of the package 10 of present disclosure may also be used to provide dual packaging systems containing two needles. In one or more embodiments, this dual packaging can help to improve work flow and efficiency for users of the two-needle technique by removing the need to remember to get two needles instead of one. In one or more embodiments, this dual packaging can also be helpful for clinicians who traditionally use a one-needle technique to fill and inject, as such practitioners may not be used to getting a separate packaged component. In one or more embodiments, this dual packaging can also help to drive compliance in clinical settings where managers want clinicians to use a two-needle technique but the clinicians would prefer to use the more convenient one-needle technique. In one or more embodiments, dual packaging can be beneficial because it helps to prevent a user from injecting a patient with a device in the fill state either accidentally or purposefully. For passive safety, injection with a device in a fill state could prevent the safety from activating. In one or more embodiments, providing two needles allows a user to perform injection with a second needle that has not been dulled, recapped, or undergone risk of touch contamination. In one or more embodiments, the two needles include a fill needle (e.g. blunt fill needle) and a needle for injection (e.g. a safety needle). In other embodiments, one or both of the needles is a conventional needle.

Figure 21:
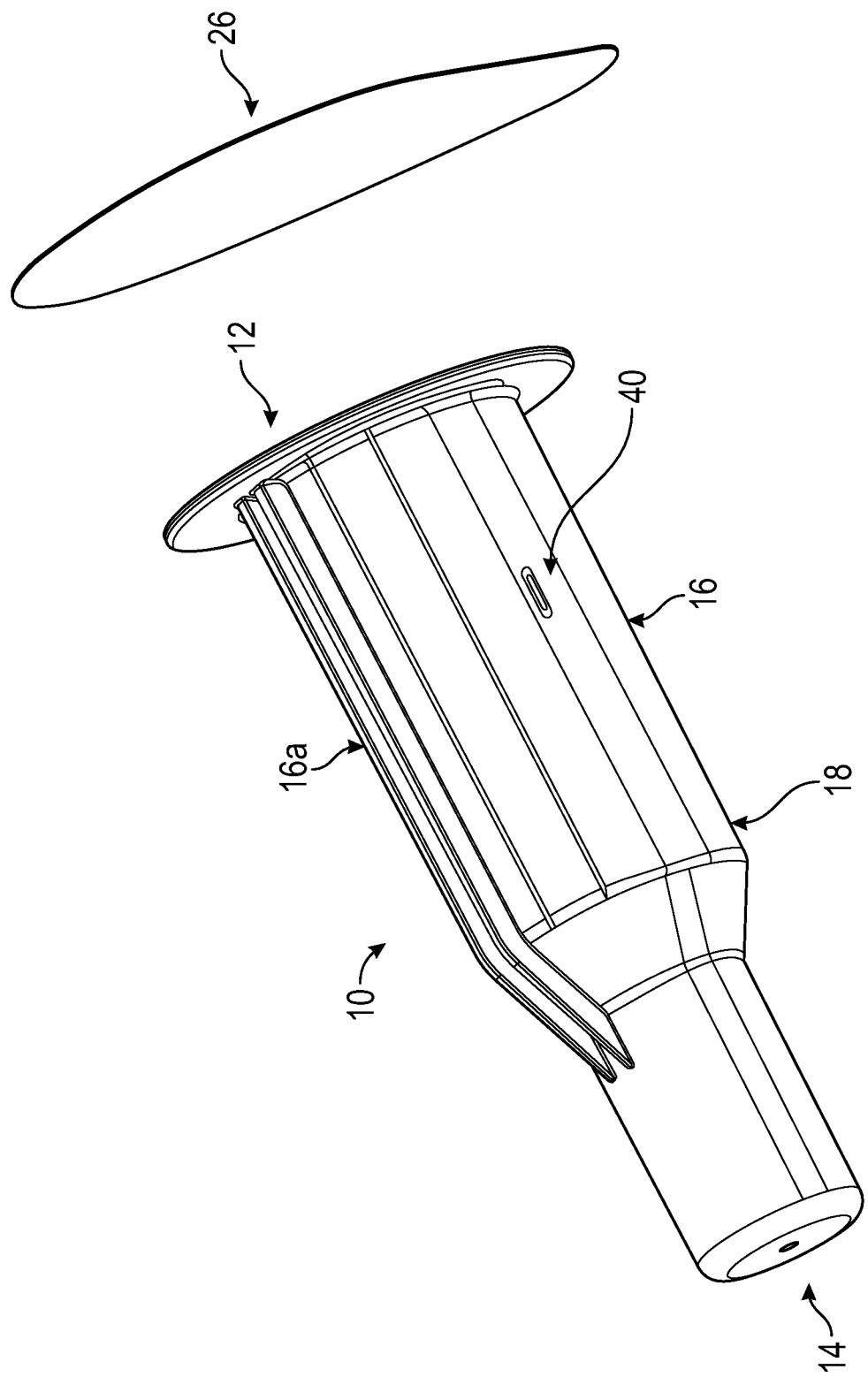
FIG. 21 illustrates an alternate embodiment of the package according to one aspect of the present disclosure having an internal retention bump.

As shown in FIG. 21, another aspect of the present disclosure pertains to a medical packaging including an open proximal end, a closed distal end, a compartment having a sidewall extending between the closed distal end and the open proximal end, one or more molded detents on an inside surface of the compartment, and a flange disposed at the open proximal end. In an alternate embodiment, as shown in FIG. 21, the interference ribs may be in the form of one or more internal retention bumps 40 disposed along the inside surface of sidewall 18. In one or more embodiments, the one or more internal retention bumps 40 may be disposed along the entirety of the length of first segment 16a of compartment 16. In one or more embodiments, the one or more internal retention bumps 40 may be disposed along a portion of the length of first segment 16a of compartment 16.

One or more alternate embodiments of the present disclosure relate to a dual compartment packaging system comprising the single compartment package 10 of the present disclosure.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein provided a description with reference to particular embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents.

What is claimed is:

1. A medical packaging comprising:
an open proximal end;
a closed distal end;
a compartment having a sidewall extending between the closed distal end and the open proximal end;
the compartment further including a first segment, a second tapered segment, and a third narrowed segment;
a plurality of interference ribs disposed on an inside surface of the compartment;
a short rib extending from the second tapered segment of the compartment, the short rib configured to interact with a corresponding slot located on a housing of a safety needle device, wherein the short rib orients the safety needle device such that it can be fully received in the compartment in one direction only; and
a flange disposed at the open proximal end;
wherein the plurality of interference ribs extend along the entire length of the inside surface from the open proximal end to the closed distal end, and the plurality of interference ribs are configured to engage a portion of a body of a safety needle device via friction-fit.

2. The medical packaging of claim 1, wherein the plurality of interference ribs extend radially inward from the sidewall and are configured to engage a portion of a fluid transfer device when the fluid transfer device is positioned within the compartment of the packaging.

3. The medical packaging of claim 1, wherein the plurality of interference ribs are disposed on the inside surface at the proximal end of the compartment.

4. The medical packaging of claim 1, further comprising one or more cavity projecting outwardly from the sidewall extending to the open proximal end in a distal direction along the inside surface of the compartment.

5. The medical packaging of claim 4, wherein one or more cavities may be disposed 1-360° apart.

6. The medical packaging of claim 5, wherein one or more cavities may be disposed 180° apart.

7. The medical packaging of claim 5, wherein the plurality of interference ribs are separated equally about a circumference of the inside surface of the one or more cavity.

8. The medical packaging of claim 4, wherein the plurality of interference ribs are oriented 180° apart around a circumference of the inside surface of the one or more cavity.

9. The medical packaging of claim 4, wherein the one or more cavity is shaped to nest a protruding segment of a body of a safety needle device.

10. The medical packaging of claim 1, wherein the plurality of interference ribs extends in a direction substantially parallel to a longitudinal axis of the compartment.

11. The medical packaging of claim 1, wherein the plurality of interference ribs have a triangular, square, rectangular, or rounded shape.

12. The medical packaging of claim 1, further comprising a removable seal that engages with the flange.

13. The medical packaging of claim 12, wherein the removable seal includes a pull tab.

14. The medical packaging of claim 12, wherein the removable seal includes graphics, symbols, diagrams, words or other instructions.

15. The medical packaging of claim 1, wherein the flange includes at least one flat edge.

16. The medical packaging of claim 1, wherein the plurality of interference ribs are arranged in sets of two or more individual ribs.

17. The medical packaging of claim 16, wherein the individual ribs comprising the one or more sets of interference ribs are spaced close together from one another.

18. The medical packaging of claim 16, wherein the individual ribs comprising the one or more sets of interference ribs are spaced apart from one another.

19. The medical packaging of claim 1, wherein the plurality of interference ribs are made from a polymeric material.

20. The medical packaging of claim 19, wherein the polymeric material is polyester, polycarbonate, polyethylene, polystyrene, polypropylene, or combinations or co-polymers thereof.

21. The medical packaging of claim 1, wherein the plurality of interference ribs are oriented opposite from each other around a circumference of the packaging.

22. The medical packaging of claim 1, wherein the short rib is disposed in an off-center orientation on the inside surface of the compartment.

23. The medical packaging of claim 1, further comprising an activation prevention element disposed on the inside surface of the compartment.

24. The medical packaging of claim 23, wherein the activation prevention element is configured to engage with a corresponding slot, notch or recess located on an activation element of a safety needle device.

25. The medical packaging of claim 23, wherein the activation prevention element is ribs protruding outwardly into the compartment.

26. The medical packaging of claim 23, wherein the activation prevention element is configured to nest a passive rotational activation element of a safety needle device.

27. The medical packaging of claim 23, wherein the activation prevention element includes a tapered leading edge.

28. The medical packaging of claim 1, further comprising a clearance between the closed distal end and a distal tip of a safety needle device when the safety needle device is fully positioned in the medical packaging.

29. The medical packaging of claim 1, further comprising at least one external rib extending radially outward from the sidewall.

30. A medical packaging comprising:
an open proximal end;
a closed distal end;
a compartment having a sidewall extending between the closed distal end and the open proximal end;
the compartment further including a first segment, a second tapered segment, and a third narrowed segment;
a plurality of interference ribs disposed on an inside surface of the compartment;
one or more molded detents on the inside surface of the compartment;
a short rib extending from the second tapered segment of the compartment, the short rib configured to interact with a corresponding slot located on a housing of a safety needle device, wherein the short rib orients the safety needle device such that it can be fully received in the compartment in one direction only; and a flange disposed at the open proximal end;
wherein the plurality of interference ribs extend along the entire length of the inside surface from the open proximal end to the closed distal end, and the plurality of interference ribs are configured to engage a portion of a body of a safety needle device via friction-fit.

\* \* \* \* \*